United States Patent
Högele et al.

(10) Patent No.: US 10,092,179 B2
(45) Date of Patent: Oct. 9, 2018

(54) SYSTEM FOR OPTICAL COHERENCE TOMOGRAPHY, COMPRISING A ZOOMABLE KEPLER SYSTEM

(71) Applicant: CARL ZEISS MEDITEC AG, Jena (DE)

(72) Inventors: Artur Högele, Oberkochen (DE);
Joachim Steffen, Westhausen (DE);
Christoph Hauger, Aalen (DE);
Holger Matz, Unterschneidheim (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 15/512,346

(22) PCT Filed: Sep. 21, 2015

(86) PCT No.: PCT/EP2015/001872
§ 371 (c)(1),
(2) Date: Mar. 17, 2017

(87) PCT Pub. No.: WO2016/041640
PCT Pub. Date: Mar. 24, 2016

(65) Prior Publication Data
US 2017/0245755 A1 Aug. 31, 2017

(30) Foreign Application Priority Data

Sep. 19, 2014 (DE) .................. 10 2014 014 182

(51) Int. Cl.
*A61B 3/10* (2006.01)
*A61B 3/13* (2006.01)
(Continued)

(52) U.S. Cl.
CPC ............ *A61B 3/102* (2013.01); *A61B 3/0091* (2013.01); *A61B 3/13* (2013.01); *G01B 9/0203* (2013.01);
(Continued)

(58) Field of Classification Search
CPC ........... A61B 3/0008; A61B 3/14; A61B 3/12; A61B 3/102; A61B 3/0025
(Continued)

(56) References Cited

U.S. PATENT DOCUMENTS

| 5,077,622 A | 12/1991 | Lynch et al. |
| 5,321,501 A | 6/1994 | Swanson et al. |

(Continued)

FOREIGN PATENT DOCUMENTS

| DE | 10 2005 031 496 A1 | 1/2007 |
| DE | 10 2005 042 436 A1 | 4/2007 |

(Continued)

OTHER PUBLICATIONS

HAAS Laser Technologies Inc., 25mm Catalog, Copyright 2009, pp. 1-46, (http://www.haaslti.com/specialty-catalogs/25mm-Series-Catalog.pdf).

(Continued)

*Primary Examiner* — Mohammed Hasan
(74) *Attorney, Agent, or Firm* — Nixon Peabody LLP; Jeffrey L. Costellia

(57) ABSTRACT

The invention relates to an optical system for examining an eye by means of optical coherence tomography. The OCT system is designed in such a way that at least a first and a second state of the optical system can be selectively set by controlling the variable optical unit. In the first state, the OCT measurement beam has a measurement focus at an object distance from the objective, wherein the object distance has a value between 50 millimeters and 400 millime- (Continued)

ters. In the second state, the measurement beam has defocusing at the same object distance, wherein the defocusing corresponds to a distance of a virtual or real focus from a position of the object distance that is greater than 100 millimeters.

21 Claims, 13 Drawing Sheets

(51) Int. Cl.
  *A61B 3/00* (2006.01)
  *G02B 21/02* (2006.01)
  *G02B 27/09* (2006.01)
  *G01B 9/02* (2006.01)

(52) U.S. Cl.
  CPC ..... *G01B 9/02035* (2013.01); *G01B 9/02091* (2013.01); *G02B 21/025* (2013.01); *G02B 27/095* (2013.01)

(58) Field of Classification Search
  USPC .................................................. 351/200–246
  See application file for complete search history.

(56) References Cited

U.S. PATENT DOCUMENTS

| | | | |
|---|---|---|---|
| 5,359,417 A | 10/1994 | Müller et al. | |
| 5,493,109 A | 2/1996 | Wei et al. | |
| 5,506,634 A | 4/1996 | Wei et al. | |
| 5,615,038 A | 3/1997 | Suzuki et al. | |
| 5,657,128 A | 8/1997 | Müller et al. | |
| 5,795,295 A | 8/1998 | Hellmuth et al. | |
| 5,975,699 A | 11/1999 | Hellmuth | |
| 5,991,090 A | 11/1999 | Strähle | |
| 6,004,314 A | 12/1999 | Wei et al. | |
| 6,095,648 A | 8/2000 | Birngruber et al. | |
| 6,212,006 B1 | 4/2001 | Reiner | |
| 6,377,349 B1 | 4/2002 | Fercher | |
| 6,409,345 B1 | 6/2002 | Molebny et al. | |
| 6,550,917 B1 | 4/2003 | Neal et al. | |
| 6,736,510 B1 | 5/2004 | Van Hengten | |
| 7,022,117 B1 | 4/2006 | Hohla et al. | |
| 7,036,934 B1 | 5/2006 | Youssefi et al. | |
| 7,241,012 B2 | 7/2007 | Mihashi et al. | |
| 7,488,070 B2 | 2/2009 | Hauger et al. | |
| 7,692,797 B2 | 4/2010 | Kawahara | |
| 7,699,468 B2 | 4/2010 | Gaida | |
| 7,761,139 B2 | 7/2010 | Tearney et al. | |
| 7,823,782 B2 | 11/2010 | Yatagai et al. | |
| 7,837,328 B2* | 11/2010 | Fukuma .............. A61B 3/102 351/200 |
| 7,839,494 B2 | 11/2010 | Reimer et al. | |
| 7,889,423 B2 | 2/2011 | Reimer et al. | |
| 7,978,404 B2* | 7/2011 | Reimer .............. A61B 90/36 359/368 |
| 8,348,429 B2* | 1/2013 | Walsh .............. A61B 3/1005 351/204 |
| 9,696,134 B2* | 7/2017 | Arieli .............. G01B 9/0203 |
| 2001/0036002 A1 | 11/2001 | Tearney et al. | |
| 2003/0160942 A1 | 8/2003 | Xie et al. | |
| 2003/0193647 A1 | 10/2003 | Neal et al. | |
| 2004/0012760 A1 | 1/2004 | Mihashi et al. | |
| 2005/0241653 A1 | 11/2005 | Van Heugten et al. | |
| 2005/0243276 A1 | 11/2005 | Van Heugten et al. | |
| 2006/0066869 A1 | 3/2006 | Ueno et al. | |
| 2006/0114411 A1 | 6/2006 | Wei et al. | |
| 2006/0152677 A1 | 7/2006 | Youssefi et al. | |
| 2007/0013918 A1 | 1/2007 | Hauger et al. | |
| 2007/0046948 A1 | 3/2007 | Podoleanu et al. | |
| 2007/0229760 A1 | 10/2007 | Hirohara et al. | |
| 2008/0117432 A1 | 5/2008 | Reimer et al. | |
| 2008/0117503 A1 | 5/2008 | Reimer et al. | |
| 2008/0117504 A1 | 5/2008 | Reimer et al. | |
| 2008/0186551 A1 | 8/2008 | Hanft et al. | |
| 2008/0198329 A1 | 8/2008 | Gaida | |
| 2008/0304144 A1 | 12/2008 | Reimer et al. | |
| 2009/0279052 A1 | 11/2009 | Hauger et al. | |
| 2010/0014156 A1 | 1/2010 | Iketaki | |
| 2010/0033676 A1 | 2/2010 | De Vries et al. | |
| 2011/0026035 A1 | 2/2011 | Muto et al. | |
| 2011/0228218 A1 | 9/2011 | Hauger et al. | |
| 2012/0002274 A1 | 1/2012 | Knoblich et al. | |
| 2012/0092615 A1 | 4/2012 | Izatt et al. | |
| 2012/0274897 A1* | 11/2012 | Narasimha-Iyer ..... A61B 3/102 351/206 |
| 2013/0141695 A1 | 6/2013 | Buckland et al. | |
| 2013/0265545 A1 | 10/2013 | Buckland et al. | |
| 2016/0081545 A1 | 3/2016 | Hauger et al. | |
| 2017/0065172 A1* | 3/2017 | Hauger .............. A61B 3/103 |

FOREIGN PATENT DOCUMENTS

| | | |
|---|---|---|
| DE | 10 2007 019 677 A1 | 5/2008 |
| DE | 10 2007 019 678 A1 | 5/2008 |
| DE | 10 2007 019 679 A1 | 5/2008 |
| DE | 10 2007 019 680 A1 | 5/2008 |
| DE | 10 2008 059 876 A1 | 5/2008 |
| DE | 10 2011 119899 | 6/2013 |
| EP | 0 697 611 | 2/1996 |
| EP | 1 918 753 | 5/2008 |
| WO | WO 2010-060622 | 6/2010 |

OTHER PUBLICATIONS

German Office Action, with translation thereof, for corresponding DE application No. 10 2014 014 182.9 dated Jun. 12, 2015.
International Search Report for PCT/EP2015/001872 dated Dec. 4, 2015.
Written Opinion for PCT/EP2015/001872.

* cited by examiner

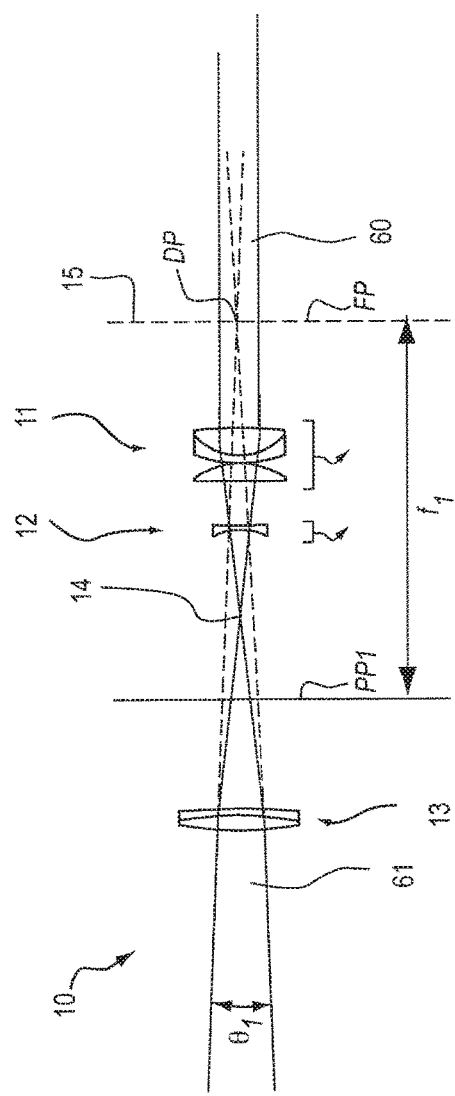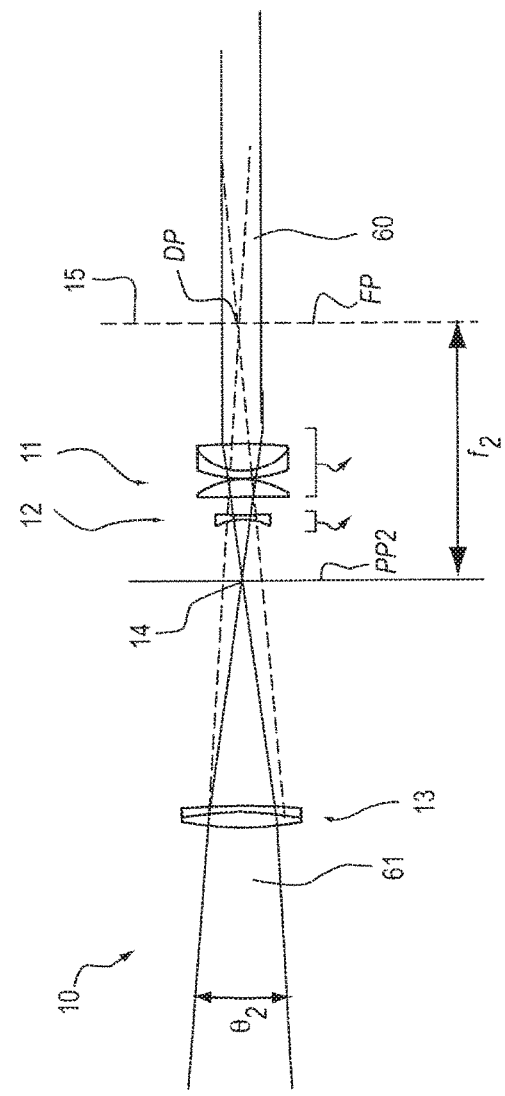

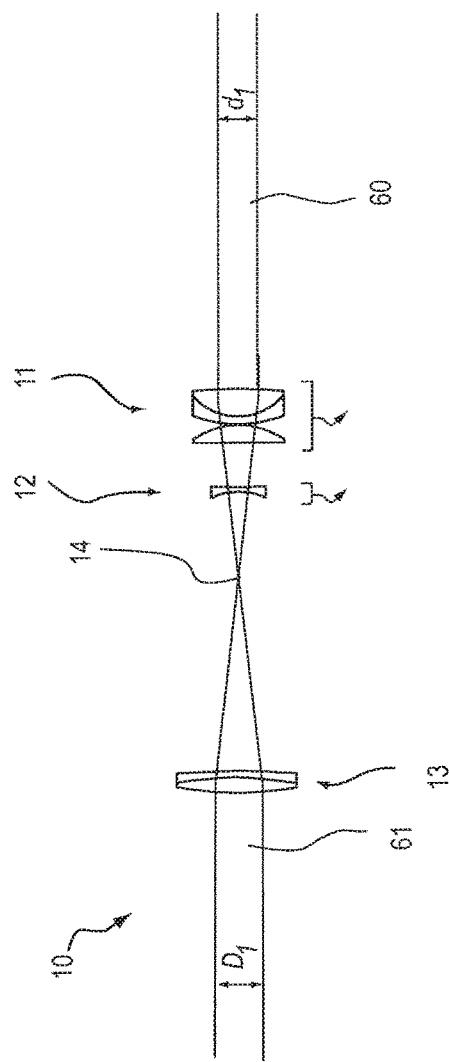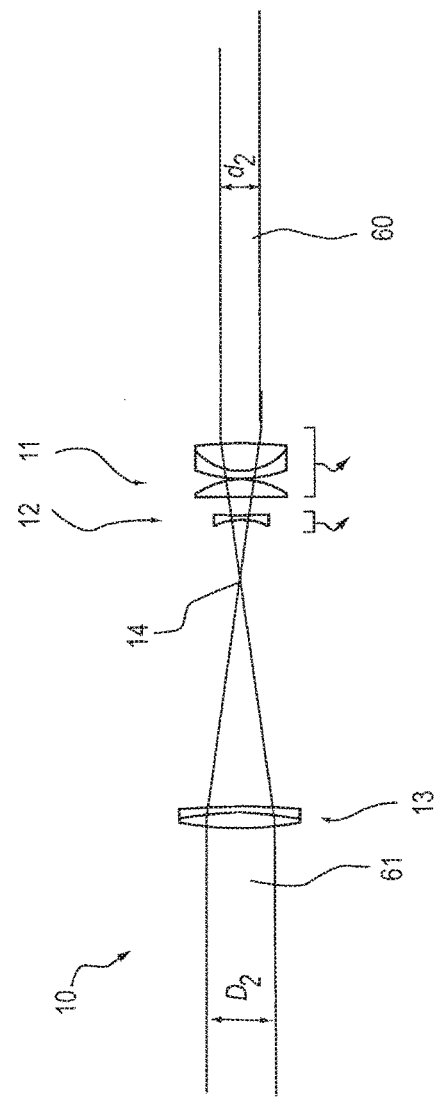

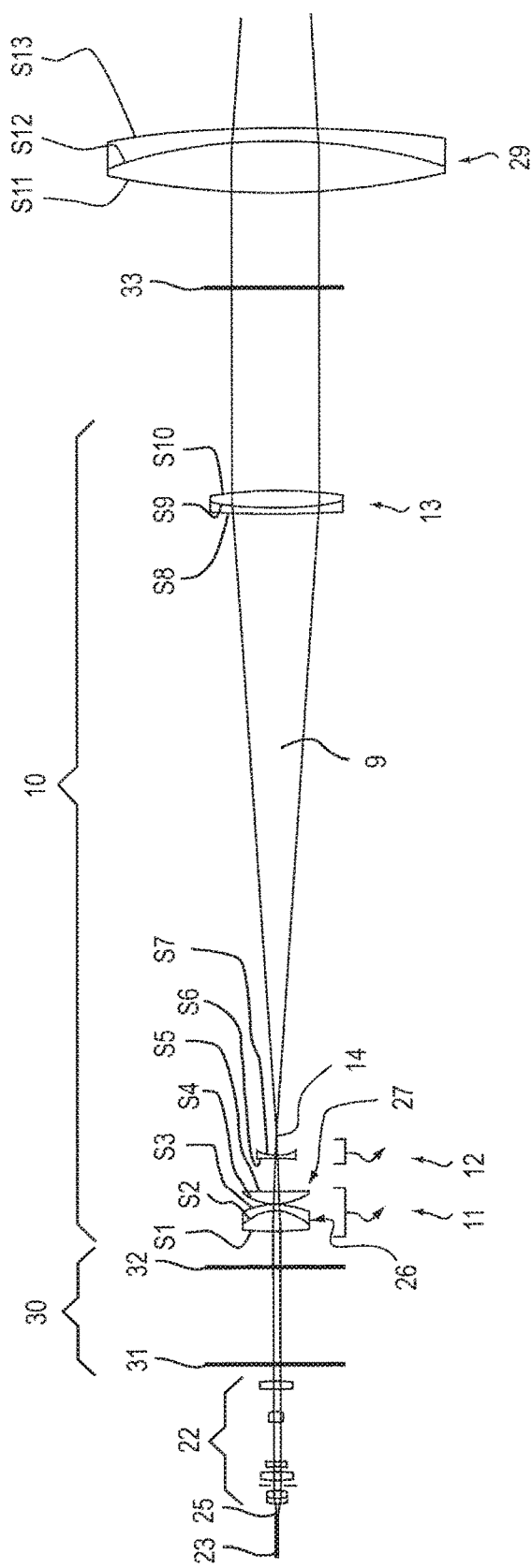

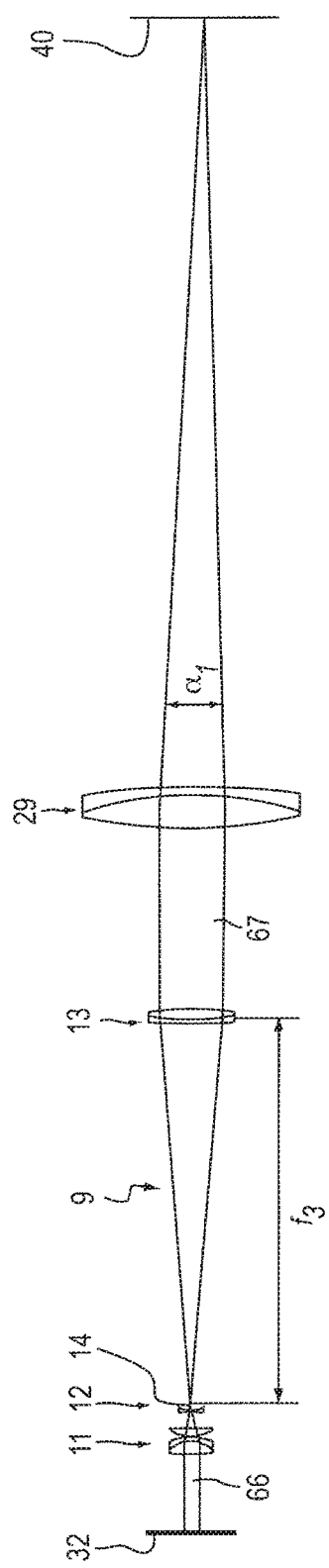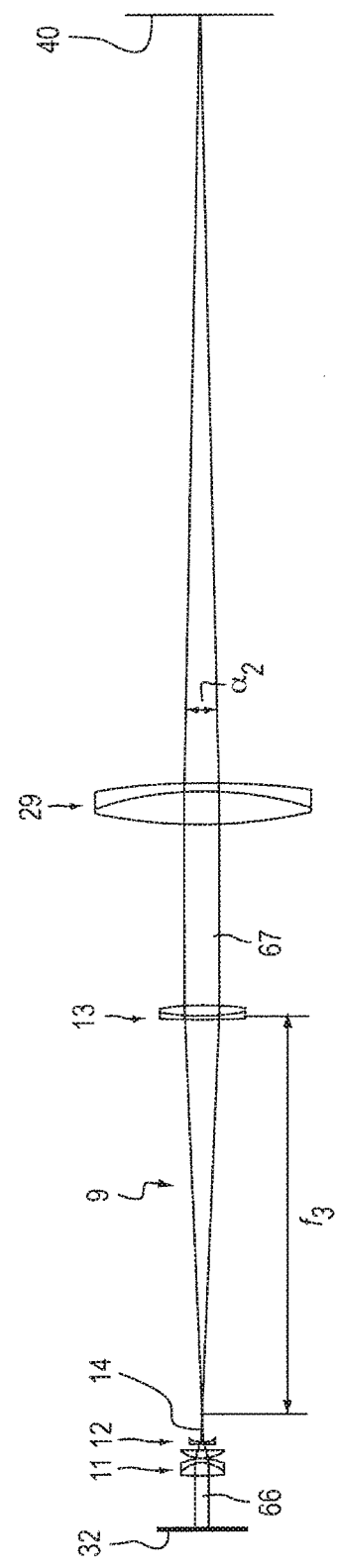

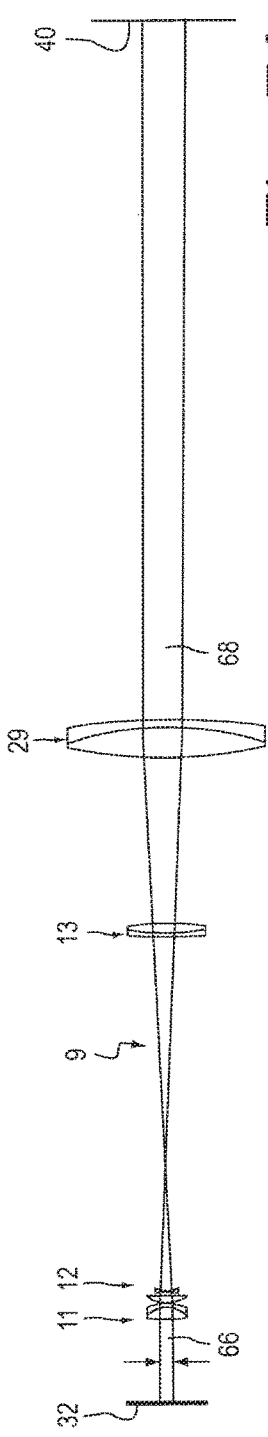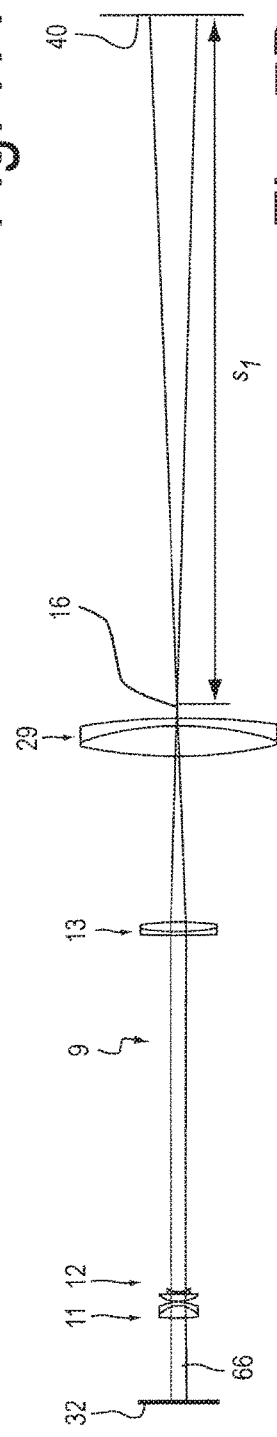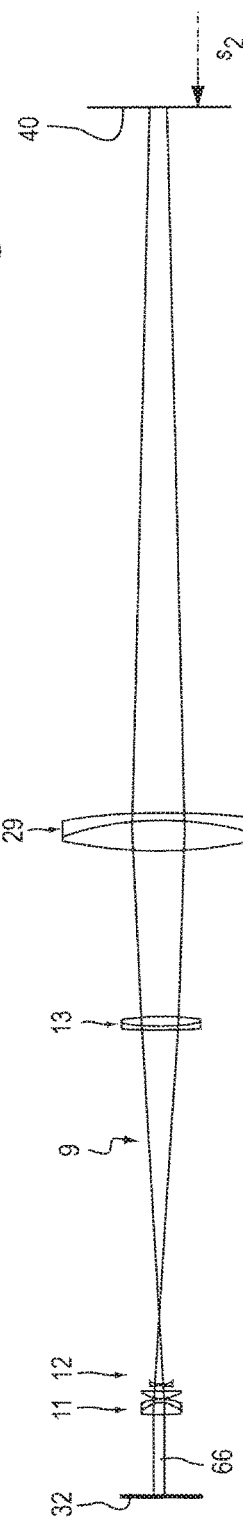

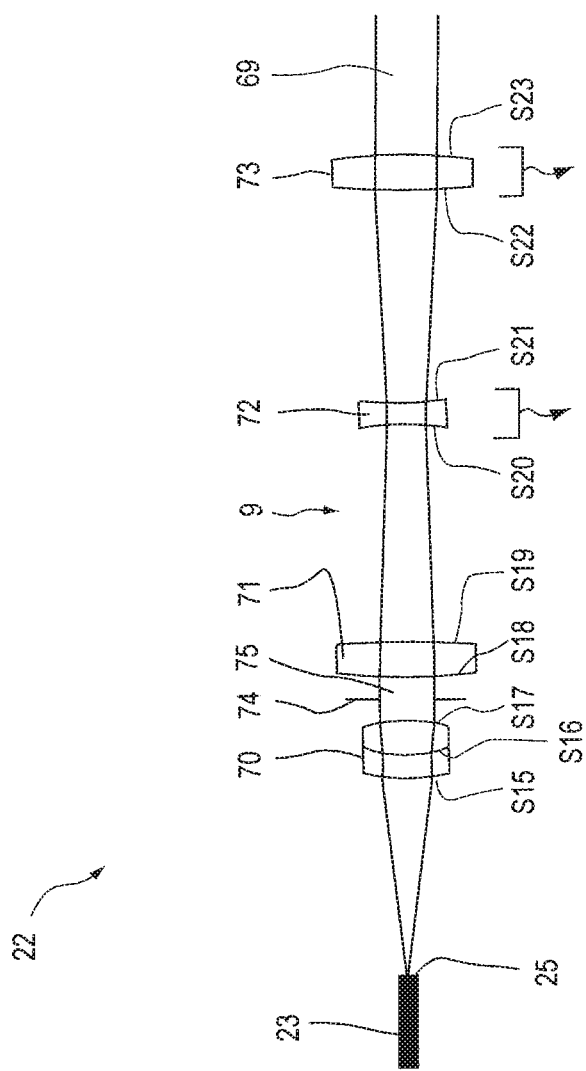

SYSTEM FOR OPTICAL COHERENCE TOMOGRAPHY, COMPRISING A ZOOMABLE KEPLER SYSTEM

CROSS-REFERENCE TO RELATED APPLICATIONS

This application claims the priority of the German patent application DE 10 2014 014 182.9, filed on Sep. 19, 2014, the entirety of which is incorporated herein by reference.

FIELD OF THE INVENTION

The present disclosure relates to an optical system for examining eyes using optical coherence tomography. In particular, the present disclosure relates to a system for optical coherence tomography, comprising a variable optical assembly, by means of which a position of the measurement focus is settable in controlled fashion along the beam axis thereof.

BACKGROUND

Optical coherence tomography (OCT) has developed to become an important noninvasive diagnostic technique on the eye. Increasingly, this method is also incorporated into the operative process. OCT allows slice or volume images of the anterior and posterior eye portions to be produced with a comparatively high resolution and virtually in real time.

An example for the frequent use of OCT in the posterior eye portion is the diagnosis of glaucoma, changes in the macula and retinal disorders. By way of example, OCT is applied in the anterior eye portion for pre-, intra- and post-operative diagnostics in the case of cataract operations.

The multifaceted possibilities for using OCT systems have led to the development of optical systems which have both a microscopy system and an OCT system integrated therein. Such systems permit OCT analysis in the field of view of the microscopy system such that the surgeon may navigate the OCT scanning region with the aid of the microscopy system. The produced OCT images may improve intraoperative orientation and diagnostics for the surgeon and therefore ensure an ideal course of the operation.

Typically, such optical systems may be operated in two configurations, with the first configuration serving to examine the anterior portion of the eye and the second configuration serving to examine the retina. In the second configuration, an additional optical assembly is usually arranged between the objective and the eye in the beam path of the microscope and of the OCT system.

In typical systems, this optical assembly is a fundus imaging system or a contact lens. A fundus imaging system consists of an ophthalmoscopy lens and a reducing lens. An intermediate image of the retina is produced between the reducing lens and the ophthalmoscopy lens by way of the ophthalmoscopy lens. With the aid of a positioning device, it is possible to position the ophthalmoscopy lens in such a way that the fundus of the eye is imaged sharply. In particular, fundus imaging systems are disadvantageous in that an unwanted eye contact by the ophthalmoscopy lens may occur during the operation. Moreover, options for illuminating the operating field by means of illumination from the operating microscope are greatly restricted when the fundus imaging system is used. Therefore, the illumination of the microscopy system is usually switched off in the case of operations in the posterior portion.

In contrast thereto, contact lenses are affixed on the cornea with the aid of a contact gel. The contact lens lifts the refractive power of the cornea. This facilitates positioning the object plane of the microscope on the retina by modifying the distance. However, the contact lens may be destabilized during the operation. Air bubbles, blood and liquid may ingress between cornea and contact lens. The consequence is that the surgical intervention has to be interrupted in order to undertake a time-consuming cleaning process.

A complicated re-equipping process is required both in the case of fundus imaging systems and in the case of contact lenses in order to change between the configuration for imaging the anterior portion and the configuration for imaging the retina. Moreover, when these systems are used, the object plane of the microscope and the scanning plane of the OCT system together are respectively arranged only in the anterior portion of the eye or only in the posterior portion of the eye. However, there are surgical interventions in which it has been found to be advantageous that an examination of the retina by means of OCT is required, but wherein the anterior portion of the eye should continue to be observed by the microscopy system. A cataract operation is an example of such a surgical intervention.

There is therefore a need for optical systems which facilitate efficient and precise carrying out of an examination or intervention on the eye.

SUMMARY

Embodiments provide an optical system for examining an eye by means of optical coherence tomography (OCT). The system may comprise an OCT system configured to produce a measurement beam which is incident on the eye. The OCT system may comprise an objective and a variable optical assembly. As seen relative to a light path of the measurement beam directed toward the object, the variable optical assembly may be disposed upstream of the objective. The OCT system may be embodied in such a way that a first state and a second state of the optical system are selectively settable by means of an actuation of the variable optical assembly or in a manner caused by the actuation of the variable optical assembly. In the first state, the measurement beam may have a measurement focus at an object distance from the objective. In the first state and in the second state, the object distance may respectively have a value of between 50 millimeters and 400 millimeters. The measurement beam may have defocusing at the same object distance in the second state. The defocusing may correspond to a distance of a virtual or real focus from a position of the object distance which is greater than 100 millimeters. A measurement beam which is parallel in the object plane represents a distance of a virtual or real focus from the object plane which is infinite, and therefore greater than 100 millimeters.

In accordance with a further embodiment, the distance of the real or virtual focus in the second state is greater than 130 millimeters, greater than 150 millimeters, greater than 170 millimeters or greater than 200 millimeters or greater than 300 millimeters or greater than 500 millimeters. In accordance with a further embodiment, the measurement beam is parallel or substantially parallel at the object distance in the second state. In accordance with a further embodiment, the variable optical assembly may be controllably settable in such a way that the variable optical assembly and the objective together form an afocal or a substantially afocal system. In the second state, the variable optical assembly and the objective together may form an afocal or substantially afocal system.

The object distance has the same value in the first state and in the second state. The eye, in particular the cornea of the eye or the front surface of the cornea, may be arrangeable at the object distance. The object distance may define a position relative to the objective and/or a position on the object side of the objective. The position of the object distance may be measured relative to a fixed reference point. Alternatively, or additionally, a position of the objective measured relative to the fixed reference point may be the same or substantially the same in the first state and in the second state. The object distance may be measured along an optical axis of the objective and/or relative to an object-side vertex of the objective. The object distance may have a value in a range between 50 millimeters and 300 millimeters or in a range between 100 millimeters and 300 millimeters or in a range between 100 millimeters and 250 millimeters or in a range between 150 millimeters and 250 millimeters. By way of example, the object distance may be 150 millimeters or 200 millimeters or 250 millimeters.

This provides an optical system which facilitates an efficient and precise examination of the eye. In particular, this allows capture of OCT data from both the anterior portion of the eye and the posterior portion of the eye, such as the retina, within a short period of time. The anterior portion of the eye may include the conjunctiva, the cornea, the lens and the iris. Here, neither the utilization of a contact lens nor the use of a fundus imaging system is required for examining the posterior portion. The optical system may be configured in such a way that a measurement focus of the measurement beam is arranged in the cornea of the eye in the first state and/or the measurement focus is arranged in the retina of the eye in the second state. The cornea may be arranged at the position of the object distance. The eye may be an emmetropic eye a non-accommodated state.

The measurement focus of the measurement beam may have a beam waist. The beam waist may be defined as that axial position along an axis of the measurement beam at which the measurement beam has the smallest diameter. The measurement focus, in particular the beam waist of the measurement focus, may be situated within the axial measurement range of the OCT system. The axial measurement range may be a region along the beam axis of the measurement beam, over which scattered intensities are capturable during a scan of the OCT system. By way of example, measurement data may be captured over the axial measurement range by changing the optical path length of the reference arm. By way of example, the change in the optical path length of a reference arm may be brought about by a modification of the position of reference mirror arranged in the reference arm.

Moreover, the OCT system facilitates a combination with a further optical component in an efficient manner. Such a further optical component may be configured to produce a light beam or a beam path which passes through the objective. The light beam or the beam path may be directed to the eye. By way of example, the further optical component may be a microscope or an aberrometer.

The OCT system may be a time-domain OCT system (TD-OCT) and/or a frequency-domain OCT system (FD-OCT). The OCT system may be a spectral-domain OCT system (SD-OCT) and/or a swept-source OCT system (SS-OCT).

The variable optical assembly may be embodied in such a way that a transition between the first state and the second state is producible by actuating the variable optical assembly. Expressed differently, it may not be required to change optical properties, further components of the OCT system, such as focal lengths, focal plane positions, refractive indices and/or radii of curvature, in order to alternate between the first state and the second state.

The optical system may comprise a controller. The controller may be signal-connected to the variable optical assembly. The variable optical assembly may be actuated dependent on control signals which are transferred from the controller to the variable optical assembly.

The objective may have a focal length which is greater than 100 millimeters or greater than 150 millimeters or greater than 200 millimeters. The focal length of the objective may be less than 500 millimeters or less than 400 millimeters or less than 300 millimeters. The objective may have a changeable focal length. In the first state and in the second state, the position of the object distance may be a focal plane of the objective in each case.

The measurement focus is arranged at the object distance in the first state. The beam waist of the measurement focus may be situated at the object distance. The position of the measurement focus or of the real or virtual focus may be measured without the presence of the eye or of an object. Thus, the distance of the real or virtual focus represents a distance through air.

Within the scope of the present disclosure, the phrase "that a component is configured such that parameter of the component is controllably settable" may be defined in such a way that the optical system comprises a controller which is signal-connected to the component. The controller may be configured in such a way that the parameter is settable dependent on control signals from the controller to the component.

The OCT system may comprise an interferometer. The OCT system may be embodied to produce the measurement beam and a reference beam. The OCT system may be configured in such a way that the measurement beam is brought to interfere with the reference beam. The optical system may be embodied in such a way that the interference is capturable by a detector of the OCT system.

Further, the OCT system may be configured in such a way that an axial measurement range in the first state differs from the axial measurement range in the second state. The measurement focus may be arranged in the axial measurement range in the first state. The retina of the eye may be situated in the axial measurement range in the second state. The modification of the axial measurement range may comprise a modification of the optical path length of the reference beam and/or of the measurement beam.

A portion of the measurement beam may extend in a light guide. The light guide may be an optical fiber. The optical fiber may be a multi-mode fiber and/or a mono-mode fiber. The light guide may have a light exit. The light guide may be embodied in such a way that the measurement beam is emitted through the light exit into a measurement beam optical assembly. The light exit may therefore form a light entry into the measurement beam optical assembly. The measurement beam optical assembly may be an imaging optical assembly. The light entry may therefore be a transition between a non-imaging optical assembly and an imaging optical assembly. The measurement beam optical assembly may be embodied and/or configurable in such a way that an image of the light entry is generable in the object region. The object region may be situated in the eye. The measurement focus of the measurement beam may be an image of the light entry. Alternatively, or additionally, the real or virtual focus, the distance of which from the position of the object distance represents the defocusing, may be an image of the light entry. The measurement beam optical assembly may comprise the variable optical assembly and the objective. The measurement beam optical assembly may comprise one or a combination of the following components: a scanning system, a collector optical assembly and a deflection element.

The variable optical assembly may comprise lenses, cemented elements and/or mirrors. An optical axis extending through the variable optical assembly may be a straight line or angled.

Relative to a light path of the measurement beam directed toward the object, the variable optical assembly may be disposed upstream or downstream of a deflection element. The deflection element may comprise a mirror and/or a beam splitter. An axis of a portion of the measurement beam which emerges from the deflection element may extend parallel or substantially parallel to the optical axis of the objective. The axis of the emergent portion may extend along or substantially along the optical axis of the objective.

In accordance with a further embodiment, the optical system further comprises a scanning system. The scanning system may be embodied for one-dimensional or two-dimensional scanning of the measurement beam or of the measurement focus. The measurement focus may be situated in the eye. Scanning may be lateral scanning, i.e. scanning at right angles relative to an axis of the measurement beam. The scanning system may be configured to scan the measurement focus, in particular the beam waist, in a scanning plane. The scanning plane may extend perpendicular or substantially perpendicular to the axis of the measurement beam. The scanning system may comprise one, two or more scanning mirrors. Each one of the scanning mirrors may be controllably pivotable about one or two axes. The variable optical assembly may be configured to image a point onto the deflection element, wherein this point is situated on a scanning mirror of the scanning system in the case of at least one scanning position of the scanning system. Alternatively, this point may be situated on the axis of a portion of the measurement beam in the case of the at least one scanning position, said portion extending between two scanning mirrors of the scanning system.

Relative to a light path of the measurement beam directed toward the object, the scanning system may be disposed upstream of the objective. Additionally, or alternatively, the scanning system may be disposed upstream or downstream of the variable optical assembly. The scanning system may be disposed upstream or downstream of the deflection element. The scanning system may be disposed downstream of the light entry into the measurement beam optical assembly and/or downstream of the light exit from the light guide. The scanning system may be disposed upstream or downstream of the collector optical assembly.

The OCT system may be embodied in such a way that, in the first state and/or in the second state, the measurement beam is incident on the scanning system in parallel or substantially in parallel. In the first state and/or in the second state, the measurement beam may be incident on the variable optical assembly in parallel or substantially in parallel on the light-source side. Alternatively, the measurement beam may be incident in convergent or divergent fashion on the light-source side in the first state and/or in the second state. The OCT system may be embodied in such a way that the measurement beam is selectively controllably incident on the variable optical assembly in parallel, in convergent fashion or in divergent fashion.

In accordance with a further embodiment, an overall optical effect, which the measurement beam experiences on the path which extends to an incidence at the object distance starting from an emergence from the variable optical assembly, is the same or substantially the same in the first state and in the second state. The overall optical effect may be understood to mean the change in the wavefront of the measurement beam at the end of the path when compared with the wavefront at the beginning of the path. In accordance with a further embodiment, the overall optical effect, which the measurement beam experiences on the path which extends to an incidence at the object distance starting from an emergence from the objective, is the same or substantially the same in the first state as in the second state. In accordance with a further embodiment, the overall optical effect, which the measurement beam experiences on the path which extends to an incidence at the object distance starting from an emergence from the objective, is zero or substantially zero in the first state and in the second state. In accordance with a further embodiment, the measurement beam in the first state and in the second state passes through air on the path which extends to the incidence at the object distance starting from the emergence from the objective. In the first state and in the second state, an overall optical effect can be the same or substantially same in the first state and in the second state along a path which extends to the incidence on the variable optical assembly starting from the light entry into the measurement beam optical assembly, starting from the light exit from the light guide and/or starting from the incidence on the collector optical assembly. A focal length and/or a focal plane position of one or both principal planes of the objective may be the same or substantially the same in the first state and in the second state. The combined optical effect of all optically effective surfaces of the objective, through which the measurement beam passes, may be described within the scope of the paraxial optics by these two principal planes of the objective.

The optical partial system of that optical path which extends to the incidence at the object distance starting from an emergence from the variable optical assembly may have a principal plane of an object-side beam output and a principal plane of a light-source side beam input. The combined optical effect of all optically effective surfaces of this optical partial system, through which the measurement beam passes, may be described within the scope of the paraxial optics by these two principal planes. By way of example, the optical partial system may consist of the deflection element and the objective. In the first state and in the second state, the focal length and/or the focal plane position of the principal plane of the object-side beam output and/or the focal length and/or the focal plane position of the light-source-side beam input may have the same value or a value which is substantially the same. The focal plane position may be measured relative to a fixed reference point.

Embodiments provide a system for examining an eye by means of optical coherence tomography. The optical system may comprise an OCT system configured to produce a measurement beam which is incident on the eye. The OCT system may comprise an objective and a variable optical assembly. As seen relative to a light path of the measurement beam directed toward the object, the variable optical assembly may be disposed upstream of the objective. The OCT system may be embodied in such a way that, at the same object distance from the objective, the measurement beam, either by means of an actuation of the variable optical assembly or in a manner caused by the actuation of the variable optical assembly, selectively (a) is settable to be substantially parallel or parallel; or (b) is settable to a defocusing which corresponds to a distance of a real or virtual focus of the measurement beam from the object distance which is less than 300 millimeters. In setting (a) and in setting (b), the object distance has the same value. In setting (a) and in setting (b), the object distance may have a value of between 50 millimeters and 400 millimeters.

This provides an optical system by means of which it is possible to examine the retina, to be precise both in the case of emmetropic eyes and in the case of eyes with a refractive error. The refractive error may be a spherical refractive error. The refractive error may be measured in diopter. The greater the absolute value of the refractive error is, the smaller the distance of the real or virtual focus must be from the position of the object distance in order to produce a measurement focus on the retina if the cornea of the eye is arranged at the object distance.

If the distance of the virtual or real focus is greater than the object distance by 200 millimeters, it is possible to focus the measurement beam onto the retina in the case of eyes with a refractive error of +5 dpt. If the distance of the virtual or real focus from the objective is less than the object distance by 200 millimeters, it is possible to focus the measurement beam onto the retina in the case of eyes with a refractive error of −5 dpt. The position of the object distance, as measured relative to a fixed reference point, may be the same or substantially the same in setting (a) and in setting (b). Alternatively, or additionally, a position of the objective measured relative to the fixed reference point may be the same or substantially the same in setting (a) and in setting (b).

In accordance with a further embodiment, the distance of the real or virtual focus in setting (b) may be less than 200 millimeters or less than 180 millimeters or less than 150 millimeters or less than 130 millimeters or less than 100 millimeters or less than 80 millimeters or less than 70 millimeters. In setting (a) and/or in setting (b), the measurement beam may in each case be incident on the variable optical assembly in parallel or substantially in parallel. The optical system may comprise a scanning system. The OCT system may be embodied in such a way that, in setting (a) and/or in setting (b), the measurement beam is incident on the scanning system in parallel or substantially in parallel.

The optical system may be embodied in such a way that the defocusing at the object distance is adjustable over a defocusing range in continuous and/or discrete fashion by means of the actuation of the variable optical assembly. The defocusing range may have settings (a) and/or (b). Actuation of the variable optical assembly may cause the discrete adjustment and/or the continuous adjustment.

The variable optical assembly may be embodied in such a way that a transition between setting (a) and setting (b) is producible by actuating the variable optical assembly. Expressed differently, it may not be required to change optical properties of further components of the OCT system in order to alternate between setting (a) and setting (b). In accordance with a further embodiment, an overall optical effect, which the measurement beam experiences on the path which extends up to an incidence at the object distance starting from an emergence from the variable optical assembly, is the same or substantially the same in setting (a) and in setting (b) In accordance with a further embodiment, the overall optical effect, which the measurement beam experiences along the path which extends up to the incidence at the object distance starting from an emergence from the objective, is the same or substantially the same in setting (a) and in setting (b). In accordance with a further embodiment, the overall optical effect, which the measurement beam experiences on the path which extends up to the incidence at the object distance starting from the emergence from the objective, is respectively zero or substantially zero in setting (a) and in setting (b). In accordance with a further embodiment, the measurement beam in setting (a) and in setting (b) passes through air up to the incidence at the object distance starting from the emergence from the objective. A focal length and/or a focal plane position of one or both principal planes of the objective may be the same or substantially the same in setting (a) and in setting (b).

In setting (a), an overall optical effect experienced by the measurement beam on the path extending up to the incidence on the variable optical assembly starting from the light exit from the light guide, starting from the light entry into the measurement beam optical assembly and/or starting from the incidence on the collector optical assembly may be the same or substantially the same as in setting (b).

The optical partial system of that optical path which extends to the incidence at the object distance starting from an emergence from the variable optical assembly may have a principal plane of an object-side beam output and a principal plane of a light-source side beam input. The combined optical effect of all optically effective surfaces of the optical partial system, through which the measurement beam passes, may be described within the scope of the paraxial optics by these two principal planes. By way of example, the optical partial system may consist of the deflection element and the objective. In setting (a) and in setting (b), the focal length and/or the focal plane position of the principal plane of the object-side beam output and/or the principal plane and/or the focal plane position of the light-source-side beam input may have the same value or a value which is substantially the same.

In accordance with a further embodiment, the defocusing at the object distance is further selectively settable by means of the actuation of the variable optical assembly in such a way that the distance of the real or virtual focus from the objective is greater than the object distance by between 50 millimeters and 150 millimeters or greater than the object distance by between 25 millimeters and 150 millimeters or greater than the object distance by between 20 millimeters and 150 millimeters.

The actuation of the variable optical assembly may cause the distance of the real or virtual focus. The distance of the real or virtual focus from the objective may be measured along the optical axis of the objective and/or relative to an object-side vertex of the objective.

Embodiments provide an optical system for examining an eye. The system may comprise an OCT system. The OCT system may be configured to produce a measurement beam which is incident on the eye. The OCT system may comprise an objective, a variable optical assembly and a collector optical assembly. The variable optical assembly may be arranged in the measurement beam between the objective and the collector optical assembly. The collector optical assembly may have a controllably changeable focal length. A diameter of a portion of the measurement beam emerging from the collector optical assembly may be modifiable by means of the controllably modifiable focal length or in a manner caused by the controllably modifiable focal length. The portion of the measurement beam may be parallel or substantially parallel prior to and after the change in diameter. The OCT system may be embodied in such a way that a defocusing of the measurement beam at the same object distance from the objective is controllably settable by means of an actuation of the variable optical assembly or in a manner caused by the actuation of the variable optical assembly. The object distance may have a value of between 50 and 400 millimeters.

The defocusing may be measured as a distance of a real or virtual focus of the measurement beam from a position of the object distance. Expressed differently, the distance of the real or virtual focus of the measurement beam from the position of the object distance is controllably settable by means of the actuation of the variable optical assembly or in a manner caused by the actuation of the variable optical assembly.

A ratio of maximum value ($\delta_{max}$) of the diameter of the portion of the measurement beam emerging from the collector optical assembly to a minimum value ($\delta_{min}$) of the diameter (i.e. the value $\delta_{max}/\delta_{min}$), the diameters being settable by means of, or in a manner caused by, an actuation of the collector optical assembly, may be greater than 1.5, greater than 1.7 or greater than 1.8 or greater than 2 or greater than 3 or greater than 3.5. The ratio may be less than 10 or less than 20 or less than 30.

The collector optical assembly may comprise a principal plane of a light-source-side beam input and a principal plane of an object-side beam output. The combined optical effect of all optically effective surfaces of the collector optical assembly, through which the measurement beam passes, may be described within the scope of the paraxial optics by these two principal planes. The collector optical assembly may be configured in such a way that a focal plane position of the principal plane of the light-source-side beam input is the same or substantially the same prior to and after the controllable modification of the focal length. A light entry into the OCT system may be arranged at the focal plane position. A light exit from a light guide of the OCT system may be arranged at the focal plane position.

In accordance with a further embodiment, the OCT system comprises a scanning system which is situated in the measurement beam between the collector optical assembly and the variable optical assembly. The OCT system may be configured in such a way that a portion of the measurement beam which is incident on the scanning system is parallel or substantially parallel or settable to be parallel or substantially parallel. The portion of the measurement beam incident on the scanning system may be parallel or substantially parallel for the various settings of the defocusing at the object distance, which are settable by means of, or in a manner caused by, the actuation of the variable optical assembly.

In accordance with a further embodiment, the collector optical assembly comprises a first movable optical unit having negative refractive power.

Within the scope of the present disclosure, the expression "refractive power" may denote a spherical "refractive power". Cylindrical refractive power or no cylindrical refractive power may be present in addition to the spherical refractive power. The refractive power may be a local refractive power or a non-local refractive power. The refractive power may be produced by rotationally symmetric spherical and/or rotationally symmetric aspherical optically effective surfaces. The optically effective surfaces which produce the refractive power may comprise one or more optically effective surfaces which have cylindrical refractive power. The optically effective surfaces which produce a refractive power may not have any cylindrical refractive power and/or not have any aspherical surfaces. Further, the labels first, second, third and fourth optical unit or movable optical unit are used within the scope of the present disclosure to distinguish the units from one another. Therefore, the label "third optical unit" for example does not specify that a first optical unit and a second optical unit have to be present.

Within the scope of the present disclosure, a movable optical unit may be defined as a component in which all optically effective surfaces of the component are moved together as a unit while maintaining the arrangement relative to one another. Expressed differently, the optically effective surfaces of the movable unit do not carry out a relative movement relative to one another during the common movement.

One or more of the movable optical units may be configured in such a way that they carry out a movement along and/or at an angle to an optical axis of the collector optical assembly. By way of example, the collector optical assembly may comprise one or more Alvarez lenses. Alternatively, or additionally, one or more of the movable optical units may be configured in such a way that they are selectively introducible into, and removable from, the measurement beam.

Alternatively, or additionally, the collector optical assembly may comprise one or more optical units which have a controllably modifiable form of a refractive or reflective surface and/or a controllably modifiable refractive index. By way of example, an optical unit may be one or a combination of a lens, a cemented element and a mirror. By way of example, the collector optical assembly may comprise one or more liquid lenses.

In accordance with a further embodiment, the collector optical assembly comprises a second movable optical unit. The second movable optical unit may have positive refractive power. The measurement beam may leave the collector optical assembly through the second movable optical unit in the light path directed toward the object. Expressed differently, the second movable optical unit may have an optically effective exit surface, through which the measurement beam in the light path directed toward the object emerges from the collector optical assembly.

In accordance with a further embodiment, the collector optical assembly comprises a first movable optical unit and a second movable optical unit. The first movable optical unit may have negative refractive power and the second movable optical unit may have positive refractive power. As seen along a light path of the measurement beam directed toward the object, the second movable optical unit may be disposed downstream of the first movable optical unit.

In accordance with a further embodiment, the collector optical assembly comprises a third optical unit. As seen relative to a light path of the measurement beam directed toward the object, the third optical unit may be disposed upstream of a first movable optical unit of the collector optical assembly. The first movable optical unit may have negative refractive power. Alternatively, or additionally, the third optical unit may be disposed upstream of second movable optical unit of the collector optical assembly. The second movable optical unit may have positive refractive power. Alternatively, or additionally, the third optical unit may be arranged between the first movable optical unit and a fourth optical unit. Alternatively, or additionally, the third optical unit may be arranged between the second movable optical unit and the fourth optical unit. Alternatively, or additionally, the third optical unit may have positive refractive power.

In accordance with a further embodiment, the collector optical assembly comprises a fourth optical unit. As seen relative to a light path of the measurement beam directed toward the object, the fourth optical unit may be disposed upstream of a first movable optical unit of the collector optical assembly. The first movable optical unit may have negative refractive power. Alternatively, or additionally, the fourth optical unit may be disposed upstream of a second movable optical unit of the collector optical assembly. The second movable optical unit may have positive refractive power. Alternatively, or additionally, the fourth optical unit may be disposed upstream of a third optical unit of the collector optical assembly. The third optical unit may have positive refractive power. Alternatively, or additionally, a portion of the measurement beam which emerges from the fourth optical unit in the light path directed toward the object may be parallel or substantially parallel. Alternatively, or additionally, the fourth optical unit may have positive refractive power. Alternatively, or additionally, the measurement beam in the light path directed toward the object may enter into the collector optical assembly through the fourth optical unit. Expressed differently, the fourth optical unit may have an optically effective entry surface, through which the measurement beam, in the light path directed toward the object, enters into the collector optical assembly. All refractive surfaces of the collector optical assembly through which the measurement beam passes may be represented by the surfaces of the first movable optical unit, the second movable optical unit, the third optical unit and the fourth optical unit.

Embodiments provide an optical system for examining an eye. The system may comprise an OCT system configured to produce a measurement beam which is incident on the eye. The OCT system may comprise an objective and a variable optical assembly. As seen relative to a light path of the measurement beam directed toward the object, the variable optical assembly may be disposed upstream of the objective. The variable optical assembly may comprise a first optical component. The first optical component may have an optically effective entry surface, through which the measurement beam, in the light path directed toward the object, enters into the variable optical assembly. The first optical component may have a focal plane of a principal plane of an object-side beam output of the first optical component. The variable optical assembly may have a first configuration and/or be controllably configurable into a first configuration, wherein a focal plane position of the first optical component is situated within the variable optical assembly in the first configuration. Alternatively, or additionally, the variable optical assembly may be controllably configurable into a second configuration. The focal plane position of the first optical component may be situated outside of the variable optical assembly in the second configuration. The first optical component may have a controllably modifiable focal length. The variable optical assembly may be switchable between the first configuration and the second configuration by means of, or in a manner caused by, the controllably modifiable focal length. The controllably modifiable focal length may be a focal length of a principal plane of the object-side beam output of the first optical component. Alternatively, or additionally, a multiplicity of different focal plane positions may be settable for a principal plane of an object-side beam output of the variable optical assembly by means of, or in a manner caused by, the controllably modifiable focal length of the first component. Alternatively, or additionally, a defocusing of the measurement beam at the object distance may be settable by means of, or in a manner caused by, the controllably modifiable focal length of the first component. Alternatively, or additionally, the optical system may be switchable between the first state and the second state by means of, or in a manner caused by, the controllably modifiable focal length of the first component. The measurement beam may be incident in parallel or substantially in parallel on the variable optical assembly in the first configuration of the variable optical assembly, in the second configuration of the variable optical assembly, in the first state of the optical system and/or in the second state of the optical system.

The first optical component may comprise a principal plane of an object-side beam output and a principal plane of a light-source-side beam input. The combined optical effect of all optically effective surfaces of the first optical component, through which the measurement beam passes, may be described within the scope of the paraxial optics by these two principal planes. The focal plane position and/or the focal length of a principal plane of the object-side beam output of the first optical component may be controllably variable.

The optically effective entry surface may for example be the surface of a lens, a cemented element or a mirror. Expressed differently, the first optical component has an optically effective surface, through which the measurement beam, in the light path directed toward the object, enters into the variable optical assembly. By way of example, optically effective surfaces may be refractive or reflective surfaces.

In the first configuration, the focal plane position of the first optical component is arranged within the variable optical assembly. The focal plane position may be a position of a real focus, which is produced when a parallel beam is incident on the variable optical assembly. The real focus may be arranged between two optical elements or within an optical element.

The expression "within the variable optical assembly" may be defined in such a way that the focal plane position is arranged on the optical axis between a vertex of the optically effective entry surface and a vertex of an optically effective exit surface of the variable optical assembly. The optically effective entry surface and exit surface may be defined relative to the light path directed toward the object. In the light path directed toward the object, the measurement beam may emerge from the variable optical assembly through the optically effective exit surface. In the first configuration, the measurement beam may form a real focus within the variable optical assembly. The real focus of the measurement beam may be arranged between two optical elements or within an optical element. By way of example, an optical element may be a lens or a cemented element.

In the second configuration, the focal plane position of the object-side principal plane of the first optical component is arranged outside of the variable optical assembly. In accordance with one embodiment, the focal plane of the first optical component is situated on the object side of the variable optical assembly in the second configuration. The second configuration of the variable optical assembly may be embodied in such a way that, in the case of an incident parallel beam or in the case of an incident parallel bundle of rays, this beam or this bundle of rays pass through the variable optical assembly without forming a real focus within the variable optical assembly. In the second configuration, the measurement beam need not necessarily be incident in parallel on the variable optical assembly.

The first optical component may consist of one or more optically effective surfaces. In particular, the first optical component may consist of one or more lenses and/or cemented elements. The first optical component may comprise a first movable optical unit and/or a second movable optical unit. The first movable optical unit may have negative refractive power. The second movable optical unit may have positive refractive power. As seen relative to the light path of the measurement beam directed toward the object, the second moveable optical unit may be disposed upstream of the first movable optical unit.

In accordance with one embodiment, the variable optical assembly is in the first configuration in the first state of the optical system. In accordance with a further embodiment, the variable optical assembly is in the second configuration in the second state of the optical system.

A transition from the first configuration of the variable optical assembly to the second configuration of the variable optical assembly may comprise a controllable modification of the modifiable focal length of the first component. Alternatively, or additionally, a transition from the first state of the optical system to the second state of the optical system may comprise a controllable modification of the modifiable focal length of the first component. The controllably modifiable focal length may be the focal length of a principal plane of an object-side beam output of the first component. In accordance with a further embodiment, the changeable focal length of the first component is greater or 1.5-times greater or two-times greater or 2.5-times greater or three-times greater in the second configuration than in the first configuration.

In accordance with one embodiment, the variable optical assembly is an afocal system or a substantially afocal system in the first configuration.

In accordance with a further embodiment, the variable optical assembly comprises a second optical component. Relative to a light path of the light beam directed toward the object, the second optical component may be disposed downstream of the first optical component. The second optical component may have positive refractive power. The second optical component may have such an embodiment that, in the first configuration, it images a point at the focal plane position of the focal plane of the first optical component at infinity or substantially at infinity on the object side. As seen relative to the light path directed toward the object, the second optical component may comprise the optically effective exit surface of the variable optical assembly. Expressed differently, the measurement beam in the light path directed toward the object may leave the variable optical assembly through the optically effective exit surface.

In accordance with one embodiment, a focal length of a principal plane of a light-source-side beam input of the second optical component is greater or 1.5-times greater or two-times greater or 2.5-times greater or three-times greater or four-times greater than the focal length of the principal plane of the object-side beam output of the first optical component.

The second optical component may comprise a principal plane of an object-side beam output and a principal plane of a light-source-side beam input. The combined optical effect of all optically effective surfaces of the second optical component, through which the measurement beam passes, may be described within the scope of the paraxial optics by these two principal planes.

In accordance with a further embodiment, the optical system further comprises a fixation light device. The fixation light device may be configured to produce a fixation point for an eye, wherein the eye, in particular the cornea of the eye, is arranged at the position of the object distance from the objective. The object distance may have a value of between 50 millimeters and 400 millimeters.

A fixation point may be defined as an object point which may be looked at by the eye. By being looked at, the fixation point is fixated centrally. An image of the fixation point is produced in the center of the foveola as a result of the central fixation. Producing the fixation point may comprise producing a real or virtual image. The real or virtual image may define or contain the fixation point.

In accordance with a further embodiment, the fixation light device is embodied to produce a fixation light which is incident at the position of the object distance. The fixation light may be defocused at the position of the object distance. The defocusing of the fixation light may correspond to a distance of a real or virtual image plane from the position of the object distance which is greater than 100 millimeters or greater than 200 millimeters or greater than 300 millimeters. The real or virtual image and/or the real or virtual fixation point may be situated in the image plane. The fixation light may pass through the objective and/or the variable optical assembly.

The optical system may be configured in such a way that, in the case of a scanning setting of the scanning system, an axis of a portion of the measurement beam which is incident at the object distance extends parallel or substantially parallel to the visual axis of the eye, with the eye being situated at the object distance and centrally fixating the fixation point.

The visual axis may be defined as the connecting straight line between the fixation point and the image point of the fixation point on the retina, with the fixation point being centrally fixated by the eye. Then, the image point is situated in the center of the foveola. Alternatively, or additionally, the visual axis may be defined or substantially defined by a direction of light beams of the fixation light at the object distance, i.e. at a position at which the light beams are incident on the cornea of the eye.

In accordance with a further embodiment, the optical system comprises a microscopy system which is configured to produce an observation channel. An image in an image plane of an object region of the eye may be producible with the aid of the observation channel, said object region of the eye being arranged in an object plane. The observation channel may pass through the objective. The object plane may be situated at the position of the object distance. The object plane may be optically conjugate to the image plane. The object plane may be a focal plane of the objective. The optical system may be embodied in such a way that bundles of rays of the observation channel which emanate from a point in the object plane are imaged at infinity or substantially at infinity by way of the objective. In other words, the bundles of rays may be parallel or substantially parallel downstream of the objective. The variable optical assembly may be without light rays which are used to produce, in an image plane, an image of the object region in the object plane. In particular, the variable optical assembly may be arranged outside of a left-hand stereoscopic observation channel and a right-hand stereoscopic observation channel of the microscopy system. In particular, only the measurement beam and/or light beams of a fixation light may pass through the variable optical assembly.

Since the object plane is arranged at the object distance and different defocusing states are settable at the object distance by means of the variable optical assembly, a surgeon may continuously observe the anterior portion of the eye with a microscope while tissue structures are examinable by means of the OCT system, both in the anterior portion of the eye and in the posterior portion of the eye. In particular, the OCT system may measure the axial length of the eye while regions of the anterior portion are continuously imageable by the microscopy system. This has been found to be advantageous, particularly when carrying out cataract operations.

The microscopy system may be a monoscopic microscopy system or a stereoscopic microscopy system. The stereoscopic microscopy system may comprise a left-hand observation channel and a right-hand observation channel. A stereoscopic image of the object region, which is arranged in the object plane, may be generable by means of the left-hand observation channel and the right-hand observation channel. The stereoscopic image may have two stereoscopic partial images. Each of the stereoscopic partial images may be an image of the object region in an image plane. The objective may be pierced by the left-hand observation channel and by the right-hand observation channel.

In accordance with one embodiment, a multiplicity of different focal plane positions may be controllably settable for a principal plane of an object-side beam output of the variable optical assembly by means of, or in a manner caused by, the actuation of the variable optical assembly.

The measurement focus is adjustable between the cornea and the retina of the eye by means of, or in a manner caused by, the different focal plane positions.

The variable optical assembly may comprise a principal plane of an object-side beam output and a principal plane of a light-source-side beam input. A focal plane may be assigned to the principal planes in each case. The two principal planes may represent the optical effect by means of which the portion of the measurement beam incident on the variable optical assembly is reshaped into the portion of the measurement beam which emerges from the variable optical assembly. The principal planes of the variable optical assembly and the respective focal lengths thereof may, together, represent all optically effective surfaces of the variable optical assembly through which the measurement beam passes. Expressed differently, the optical effect of all optically effective surfaces of the variable optical assembly, through which the measurement beam passes, may be described within the scope of the paraxial optics by the two principal planes and their respective focal lengths.

The focal plane of a principal plane may be defined as a plane perpendicular to the optical axis which contains the focus of this principal plane. The focal plane may be a real focal plane or a virtual focal plane. A virtual focal plane may be defined as a plane containing a virtual focus.

A parallel bundle of rays incident on the variable optical assembly on the light-source side may be reshaped by the variable optical assembly into a bundle of rays emerging from the variable optical assembly such that the emerging bundle of rays has a real or virtual focus in a focal plane of the principal plane of the object-side beam output. Accordingly, a bundle of rays incident on the light-source side, which has a virtual or real focus in a focal plane of the principal plane of the light-source-side beam input, may be reshaped into a parallel bundle of rays, which emerges from the variable optical assembly on the object side, by the variable optical assembly.

The focal plane position may be an axial position of the focal plane, measured relative to the optical axis. The focal plane position may be measured relative to a fixed reference point. The position of the principal plane may change without there being a change in the focal plane position. As a result, it is also possible for the focal length of the principal plane to change without there being a change in the focal plane position.

An axial position of a measurement focus of the measurement beam, measured relative to the beam axis of the measurement beam, may be dependent on the focal plane position for the principal plane of the object-side beam output of the variable optical assembly. This focal plane may be imaged into a plane in which the measurement focus, in particular the beam waist, is arranged by part of the measurement beam optical assembly and/or by optically effective constituents of the eye. The optically effective constituents may comprise the cornea and/or the natural lens of the eye. The defocusing of the measurement beam at the object distance, in particular the distance of the real or virtual focus from the object distance, which represents the defocusing, may be controllably settable by means of the controllable setting of the focal plane position of the principal plane of the object-side beam output of the variable optical assembly or in a manner caused by the controllable setting of the focal plane position. Alternatively, or additionally, this allows the measurement focus to be positionable at the object distance. In particular, the actuation of the variable optical assembly for selectively setting the first state, the second state, setting (a), setting (b) and/or different defocusing at the object distance may comprise the controllable setting of the focal plane position.

In accordance with a further embodiment, the optical system may be configured in such a way that a focal length of a principal plane of an object-side beam output of the variable optical assembly is controllably settable to different values. A focal plane position of the principal plane may be the same or substantially the same for each value of the focal length. The variable optical assembly may be configured as a variable beam widening device.

In the case of the same, or substantially the same, focal plane position of the principal plane of the object-side beam output, a smaller absolute value (i.e. smaller in terms of magnitude) of the focal length may cause an increase in the aperture angle of the measurement beam emerging from the variable optical assembly on the object side. A consequence of this may be that the measurement beam at the measurement focus has a larger numerical aperture. The larger numerical aperture, in turn, may have as a consequence that the diameter of the waist is reduced in the measurement focus. OCT data may be captured with a higher lateral resolution by way of a smaller diameter of the beam waist. The lateral resolution may be the resolution in a plane perpendicular to the axis of the measurement beam.

In accordance with a further embodiment, the variable optical assembly may be controllably settable into a multiplicity of afocal or substantially afocal configurations. The afocal configurations may have different values of an afocal beam widening.

The afocal beam widening may be related to a light path directed toward the object. Expressed differently, the afocal beam widening may be defined as a ratio of a diameter of a parallel bundle of rays (D) emerging from the variable optical assembly on the object side to a diameter of a parallel bundle of rays (d) incident on the variable optical assembly on the light-source side. That is to say, the afocal beam widening may be calculated as D/d.

The optical system may be embodied in such a way that the afocal beam widening is continuously and/or discretely settable over an adjustment range which has values that are less than 4 and greater than 4.5. Alternatively, the adjustment range may have values which are less than 3 and greater than 4.5. Alternatively, the adjustment range may have values which are less than 2.5 and greater than 4.5. Alternatively, the adjustment range may have values which are less than 2 and greater than 5. Alternatively, the adjustment range may have values which are less than 6 and greater than 7. Alternatively, the adjustment range may have values which are less than 5 and greater than 8. Alternatively, the adjustment range may have values which are less than 4.5 and greater than 9.

The optical system may be configured in such a way that, by means of, or in a manner caused by, the actuation of the variable optical assembly, a numerical aperture of the portion of the measurement beam running toward the measurement focus is continuously and/or discretely settable over an adjustment range which has values less than or equal to 0.02 and has values greater than or equal to 0.03. Alternatively, the adjustment range may have values less than or equal to 0.01 and may have values greater than or equal to 0.04. Alternatively, the adjustment range may have values less than or equal to 0.005 and may have values greater than or equal to 0.08.

A ratio of a maximum value ($\alpha_{max}$) of the numerical aperture to a minimum value ($\alpha_{min}$) of the numerical aperture (i.e. the value $\alpha_{max}/\alpha_{min}$), which is settable by means of, or in a manner caused by, an actuation of the variable optical assembly, may be greater than 1.5, greater than 1.7 or greater than 1.8 or greater than 2 or greater than 4. The ratio may be less than 10 or less than 20 or less than 30.

In accordance with a further embodiment, the optical system is configured or configurable in such a way that the measurement beam is incident on the variable optical assembly as a parallel or substantially parallel beam.

In accordance with one embodiment, the variable optical assembly comprises a first movable optical unit. The first movable optical unit may have negative refractive power.

Each of the movable optical units of the variable optical assembly may be configured in such a way that they carry out a movement along and/or at an angle to an optical axis of the variable optical assembly. By way of example, the variable optical assembly may comprise one or more Alvarez lenses. Alternatively, or additionally, one or more of the movable optical units may be configured in such a way that they are selectively introducible into, and removable from, the measurement beam. The movable optical units may in each case be movable dependent on control signals of a controller. Each of the movable optical units may be drive-connected to one or more actuators. The optical system may comprise a controller which is signal-connected to the actuators. The movable optical units may be movable dependent on control signals which are transferred from the controller to the one actuator or to the plurality of actuators.

The movable optical units may be moved, in particular, (a) when setting different focal plane positions of the principal plane of the object-side beam output of the variable optical assembly, (b) when setting the focal length of this principal plane and/or (c) when setting the variable optical assembly into one of the afocal configurations. In so doing, a plurality of movable optical units may carry out a relative movement relative to one another.

Alternatively, or additionally, the variable optical assembly may comprise one or more optical units which have a controllably modifiable form of a refractive or reflective surface and/or a controllably modifiable refractive index. By way of example, an optical unit may be one or a combination of a lens, a cemented element and a mirror. By way of example, the variable optical assembly may comprise one or more liquid lenses.

In accordance with a further embodiment, the variable optical assembly comprises a first movable optical unit and a second movable optical unit. The first movable optical unit and the second movable optical unit may be movable relative to one another in a controllable manner.

In accordance with a further embodiment, the first movable optical unit has negative refractive power and the second movable optical unit has positive refractive power. The refractive power may be understood to mean spherical refractive power.

In accordance with a further embodiment, the measurement beam in the light path directed toward the object enters into the variable optical assembly through the second movable optical unit. Expressed differently, the second movable optical unit has an optically effective entry surface, through which the measurement beam enters into the variable optical assembly.

In accordance with a further embodiment, the first movable optical unit is disposed downstream of the second movable optical unit, as seen relative to a light path of the measurement beam directed toward the object.

In accordance with a further embodiment, the variable optical assembly comprises a third optical unit. As seen relative to a light path of the measurement beam directed toward the object, the third optical unit may be disposed downstream of a first movable optical unit. The first movable optical unit may have negative refractive power. Alternatively, or additionally, the third optical unit may be disposed downstream of a second movable optical unit. The second movable optical unit may have positive refractive power. Alternatively, or additionally, the measurement beam along the light path directed toward the object may leave the variable optical assembly through the third optical unit. Alternatively, or additionally, the third optical unit may have positive refractive power. Alternatively, or additionally, a position of a focal plane of a principal plane of a light-source-side beam input of the third optical unit may be arranged within the variable optical assembly. The third optical unit may have an optically effective exit surface, through which the measurement beam in the light path directed toward the object leaves the variable optical assembly.

The variable optical assembly may comprise a fourth optical unit. The fourth optical unit may be arranged between the first movable optical unit and the third optical unit. The fourth optical unit may have positive or negative refractive power. The fourth optical unit may be a field lens.

In accordance with a further embodiment, the second movable optical unit comprises two separate optical subunits. The separate subunits may each have positive optical refractive power. The subunits may be spaced apart from one another.

By way of example, a subunit may be one or a combination of a lens, a cemented element or a mirror. The light-source-side optical subunit may be embodied as a cemented element. The object-side optical subunit may be embodied as a lens.

BRIEF DESCRIPTION OF THE FIGURES

The features above and further advantageous features will emerge more clearly from the following detailed description of the exemplary embodiments, where reference is made to the attached drawings. It is emphasized that not all possible embodiments necessarily obtain all or some of the advantages specified here.

FIGS. 4A and 4B illustrate how the numerical aperture of the OCT measurement beam at the measurement focus is settable by modifying a focal length in the case of a constant focal plane position for an object-side principal plane of the variable optical assembly shown in FIG. 1;

FIGS. 4C and 4D illustrate different configurations of the variable optical assembly, shown in FIG. 1, of the OCT system, by means of which different values of afocal beam widening are produced;

FIG. 5 illustrates the design of the variable optical assembly of the OCT system shown in FIG. 1;

FIGS. 6A and 6B illustrate different afocal configurations of the variable optical assembly of the OCT system shown in FIG. 1, by means of which different values of the numerical aperture are producible in the object plane;

FIGS. 7A to 7C illustrate different configurations of the variable optical assembly of the OCT system shown in FIG. 1, by means of which different defocusing states of the OCT measurement beam are producible in the object plane;

FIG. 8 illustrates the design of the collector optical assembly shown in FIG. 1;

DESCRIPTION OF EXEMPLARY AND ILLUSTRATIVE EMBODIMENTS

Figure 1:
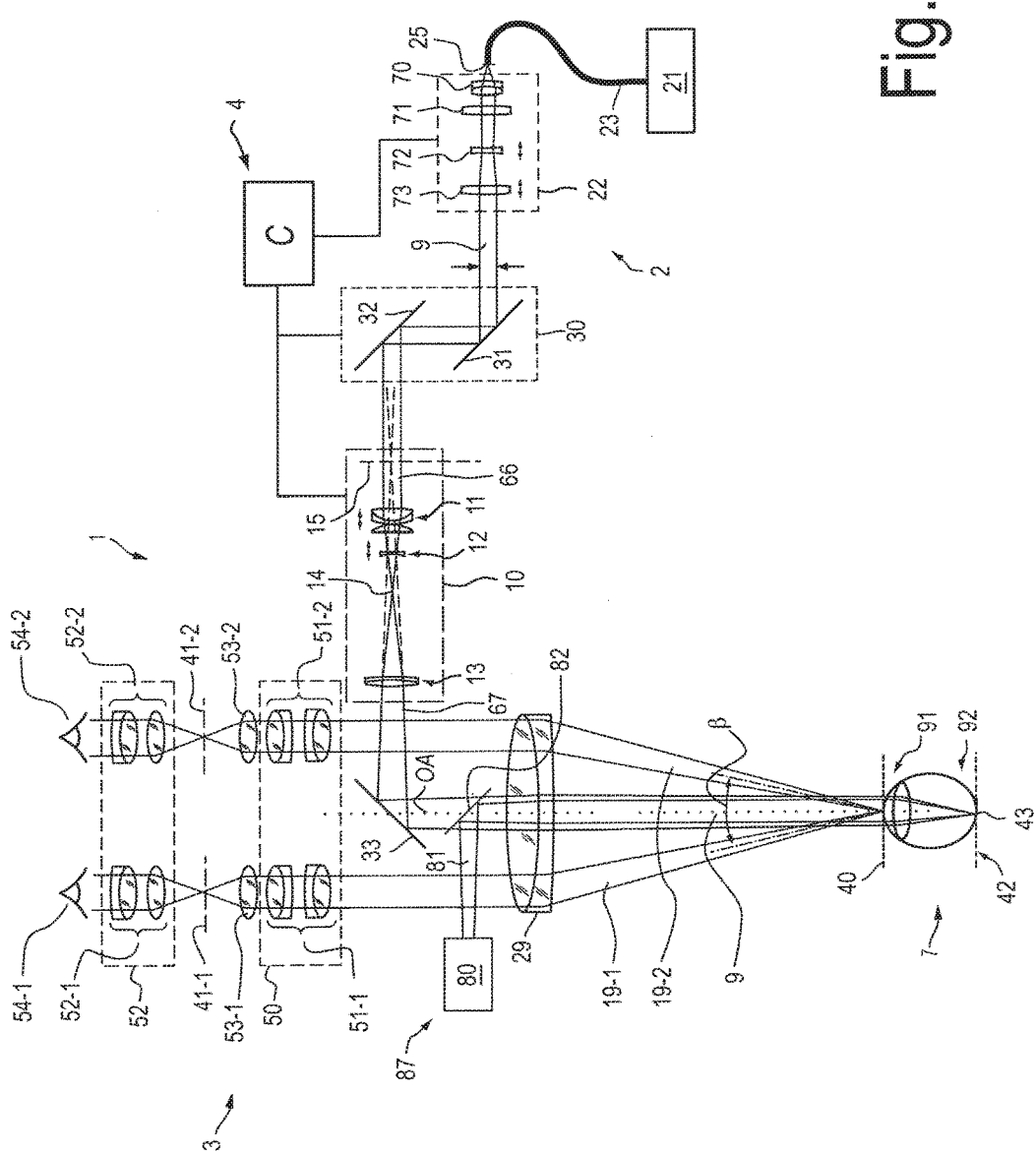
FIG. 1 is a schematic view of an optical system in accordance with an exemplary embodiment.

FIG. 1 is a schematic illustration of an optical system 1 in accordance with an exemplary embodiment. The optical system 1 comprises an OCT system 2 and a microscopy system 3. The microscopy system 3 is embodied as a stereoscopic microscope. However, it is also conceivable for the microscopy system 3 to be embodied as a monoscopic microscope. The microscopy system 3 is configured to produce two observation channels 19-1, 19-2, the axes of which intersect at a stereo angle β in the object plane 40. Each of the stereoscopic observation channels 19-1, 19-2 produces a stereoscopic partial image of the object region arranged in the object plane 40 of the microscopy system 3 in an image plane 41-1, 41-2 of the respective observation channel 19-1, 19-2.

A bundle of rays of the first observation channel 19-1 or of the second observation channel 19-2, which emanates from a point in the object plane 40, is transformed by way of an objective 29 of the microscopy system 3 into a bundle of rays which is parallel or substantially parallel. The microscopy system 3 further comprises a variable optical assembly 50 which is disposed downstream of the objective 29 in the beam path of the observation channels 19-1, 19-2. The variable optical assembly 50 comprises two zoom components 50-1, 50-2, which are each passed through by the beams of one of the observation channels 19-1, 19-2.

Each of the two zoom components 50-1, 50-2 may be embodied as an afocal optical system.

The microscopy system 3 in each case has a focusing optical assembly 53-1, 53-2 for each one of the observation channels 19-1, 19-2. For each one of the observation channels 19-1, 19-2, the focusing optical assembly 53-1, 53-2 is configured to focus bundles of rays of the respective observation channel 19-1, 19-2 emitted by a point in the object plane 40 onto a point in the image plane 41-1, 41-2. Hence, the image planes 41-1, 41-2 are optically conjugate to the object plane 40.

Further, the microscopy system 3 comprises an eyepiece 52-1, 52-2 for each one of the observation channels 19-1, 19-2. The partial images produced in the image planes 41-1, 41-2 are observable through the eyepieces 52-1, 52-2 by the eyes 54-1, 54-2 of an observer. Additionally, or alternatively, it is conceivable for the optical system 1 to comprise one or more image sensors (not shown in FIG. 1). The image sensor may be arranged in one of the image planes 41-1, 41-2 or in a plane optically conjugate thereto. The image sensor may be configured to capture one of the produced partial images.

The OCT system 2 comprises an interferometer which produces a measurement arm and a reference arm. The interferometer makes light which has passed through the measurement arm interfere with light which has passed through the reference arm.

The OCT system 2 produces a measurement beam 9 which is guided along the measurement arm to the eye 7 in a light direction directed toward the object. Scattered light of the measurement beam 9 is guided back along the measurement arm in a reversed direction, said reversed direction being reversed in relation to the light direction directed toward the object. The light which is guided back is made to interfere with the light which has passed through the reference arm.

A measurement beam optical assembly of the OCT system 2 shapes the measurement beam 9 in such a way that the measurement beam forms a measurement focus 43 in the eye 7. The light of the measurement beam 9 is produced in an OCT unit 21 and transported to the measurement beam optical assembly by way of a light guide 23. The light of the measurement beam 9 is emitted into the measurement beam optical assembly through a light exit surface 25 situated at one end of the light guide 23. The light exit surface 25 therefore forms a light entry into the measurement beam optical assembly. The measurement beam optical assembly is an imaging optical assembly configured in such a way that the portion of the measurement beam 9 which is incident on the eye 7 is settable as a parallel beam, a substantially parallel beam, as a convergent beam and/or as a divergent beam. As a result, the measurement focus 43 of the measurement beam may be produced at a selected place in the interior of the eye 7 in order to capture OCT data from a selected location in the interior of the eye. The measurement focus is an image of the light entry.

In particular, this renders it possible that the measurement focus may be positioned in a mid-region between the cornea and the retina. Then, OCT data may be captured by setting the axial measurement range in such a way that the latter extends from the cornea to the retina. The axial length of the eye to be examined may be determinable dependent on these OCT data.

Alternatively, the axial length of the eye may be determined by virtue of, initially, OCT data of the anterior portion of the eye being captured. Then, in a manner caused by the actuation of the variable optical assembly, the measurement focus is displaced from the anterior portion to the retina.

Then, OCT data of the retina are captured. Then, the axial length of the eye may be determined dependent on the OCT data of the anterior portion, the OCT data of the retina and, further, dependent on the path along which the measurement focus was displaced.

By contrast, a precise measurement of the axial length of the eye using a fundus imaging system or a contact lens is only possible with difficulties since the path difference between the reference arm and the measurement arm emerging from the additionally inserted optical elements needs to be taken into account. Moreover, higher measurement inaccuracies may arise as a result of the optical aberrations of these elements.

The anterior chamber depth is a further parameter which is measurable with high accuracy with the aid of the OCT system and the determination of which is often used for determining the intraocular lens. This parameter too is measurable with high precision as a result of the axial displaceability of the measurement focus. The positionability of the measurement focus 43 on the retina 77 of the eye 7 further facilitates being able to use a measurement light scattered at the retina 77 for the purposes of aberrometric measurements. To this end, the optical system may comprise an aberrometric measurement system (not shown in FIG. 1).

The measurement beam optical assembly comprises a collector optical assembly 22, a scanning system 30, a variable optical assembly 10, a deflection element 33 and the objective 29. The collector optical assembly 22 is configured or controllably configurable in such a way that a portion 10 of the measurement beam which emerges from the collector optical assembly 22 is parallel or substantially parallel. The collector optical assembly 22 may be embodied as a collimator lens. Alternatively, the collector optical assembly 22 may be embodied as a variable optical assembly, wherein a convergence or divergence of a portion of the measurement beam 9 emerging from the collector optical assembly 22 is settable. Alternatively, or additionally, the collector optical assembly 22 may be configured in such a way that a diameter of a parallel or substantially parallel portion of the measurement beam 9 emerging from the collector optical assembly 22 is controllably settable by the collector optical assembly 22 such that the portion of the measurement beam 9 is parallel or substantially parallel prior to and after the modification of the diameter. The design of the collector optical assembly 22 is explained with reference to FIGS. 8 and 9.

The scanning system 30 is configured to laterally scan the measurement focus 43 in two dimensions. As a result, the measurement focus 43 is moved in a scanning plane 42. The scanning system 30 comprises two scanning mirrors 31, 32, each of which is mounted in a pivotable manner. The mirrors may be drive-connected to a piezo-drive and/or to a galvanometer drive.

Figure 2A:
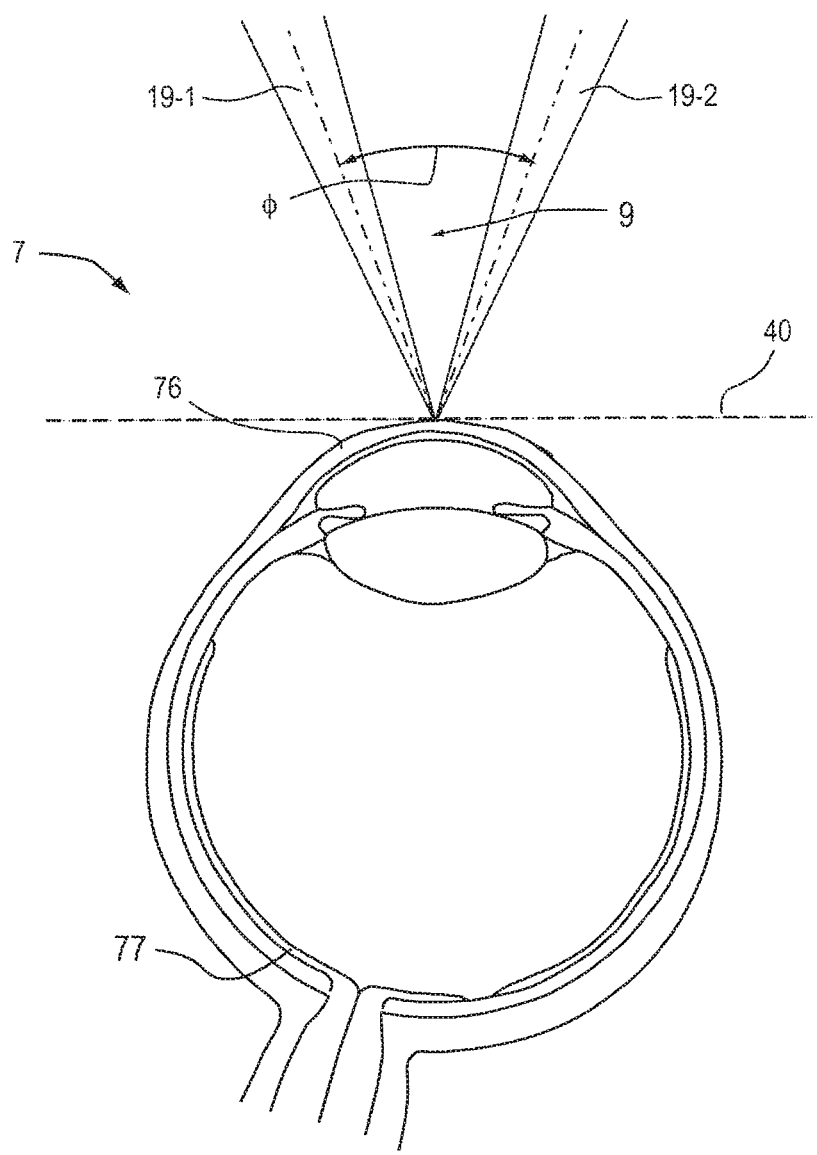
FIG. 2A illustrates the observation channels of the microscopy system in the region of the object plane when examining the anterior portion through the microscopy system shown in FIG. 1.

For the optical system 1 shown in FIG. 1, FIG. 2A illustrates the extents of the observation channels 19-1 and 19-2 of the microscopy system on the eye 7 in detail. The object plane 40 of the microscope is arranged on the front surface of the cornea 76. The object plane 40 corresponds to the front focal plane of the objective 29 (shown in FIG. 1). The front focal plane of the objective 29 is the focal plane which is situated on that side which is closer to the object. The bundles of rays of the observation channels 19-1 and 19-2 emanate from the object plane 40, and so the axes of the observation channels 19-1 and 19-2 form a stereo angle β.

As described in detail with reference to the following figures, the OCT system is configured in such a way that, in a manner caused by an actuation of the variable optical assembly 10 (shown in FIG. 1), the axial position of the measurement focus of the measurement beam, as measured relative to the axis of the measurement beam, and the beam waist diameter of the measurement focus are controllably modifiable. This has been found to be very advantageous. Firstly, this allows setting the axial position of the measurement focus and of the beam waist diameter independently of the position of the object plane of the microscopy system. As a result, the OCT system may be adapted for an examination of a specific region of the eye, wherein the object plane may remain in the anterior portion of the eye. In particular, this allows the measurement focus to be selectively positioned in the anterior portion of the eye or on the retina of the eye. This facilitates an efficient examination of different regions of the eye, wherein the anterior portion of the eye may remain under constant observation by the medical practitioner. it has been found that this may be very advantageous, particularly when carrying out cataract operations.

In particular, it has been found that anatomical parameters of the eye measured during a cataract operation after the natural lens was removed and before the intraocular lens was inserted may be used to determine the effect of the intraocular lens to be inserted with high reliability.

Furthermore, the optical system facilitates dispensing with the use of contact lenses and fundus imaging systems, as a result of which the disadvantages accompanied by the use of such systems are avoided.

Figure 2B:
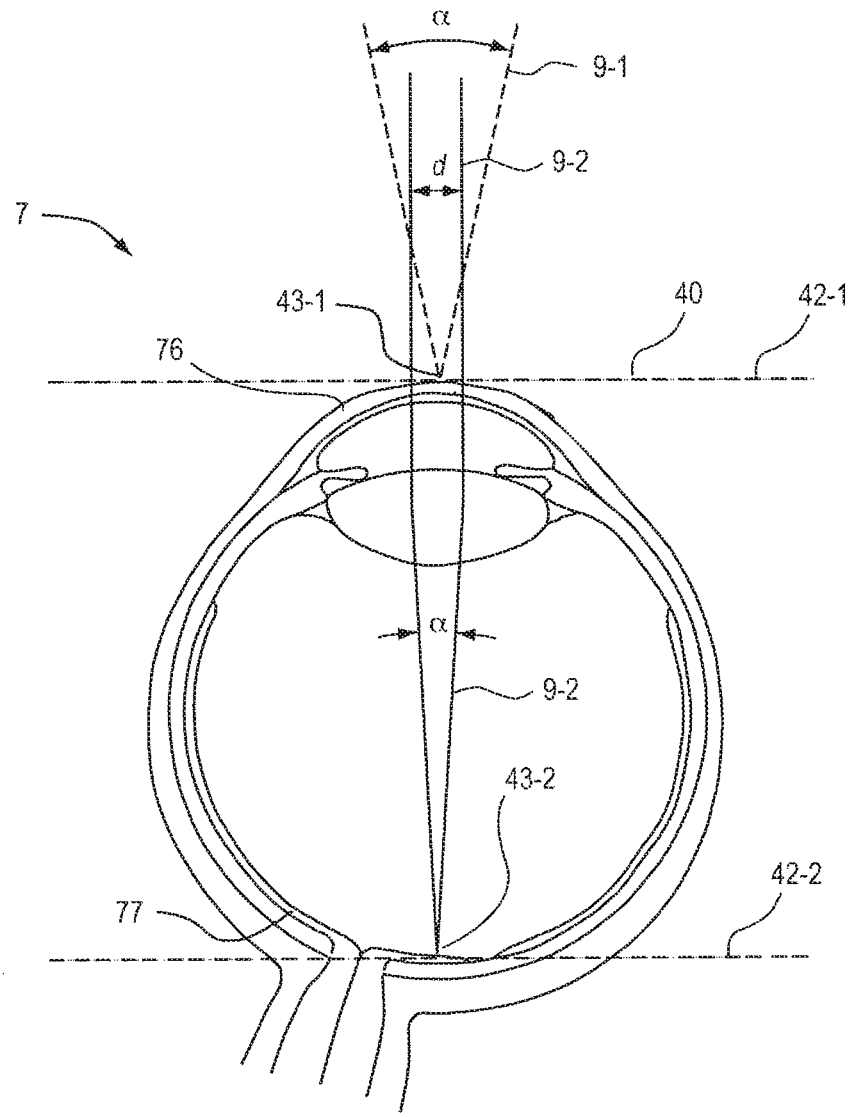
FIG. 2B illustrates how the measurement focus of the OCT beam may be selectively positioned at the object plane or on the retina of the eye by means of actuating the variable optical assembly shown in FIG. 1.

The adjustment of the axial position of the measurement focus is explained with reference to FIG. 2B. The OCT system may be brought into a first state and into a second state in a manner caused by an actuation of the variable optical assembly. In FIG. 2B, the measurement beam is denoted by reference sign 9-1 in the first state and the measurement focus is denoted by reference sign 43-1 in the first state. The measurement focus 43-1 is arranged in the object plane 40 in the first state. The measurement focus 43-1 is then situated in the front focal plane of the objective 29 (shown in FIG. 1). The scanning plane 42-1 of the measurement focus 43-1 is situated in the object plane 40. To this end, the variable optical assembly must be configured in such a way that the measurement beam is incident on the objective as a parallel or substantially parallel beam. Since portion 66 (shown in FIG. 1) of the measurement beam 9, which is incident on the variable optical assembly, is configured as a parallel beam, the variable optical assembly must be configured as a confocal system in the first state. By way of example, it is possible, in this first state, to undertake OCT measurements of a part of the region imaged by the microscopy system. By way of example, this allows OCT data representing a cross section of a region of the cornea to be captured.

In FIG. 2B, the measurement beam is denoted by reference sign 9-2 in the second state and the measurement focus is denoted by reference sign 43-2 in the second state. The measurement beam 9-2 has defocusing in the object plane 40 in the second state. The defocusing corresponds to a distance of a virtual or real focus from the object plane 40. The distance of the virtual or real focus is measured as a path through air, i.e. without the presence of the eye. In the second state, which is illustrated in FIG. 2b, this distance is infinite; i.e., the measurement beam 9-2 is incident on the object plane 40 as a parallel beam. If the eye 7 is emmetropic and not accommodated, the measurement beam 9-2 is focused onto the retina 77 of the eye 7. This facilitates capturing OCT data of regions of the retina 77. In the process, the object plane 40 remains at the cornea 76.

Therefore, the anterior region of the eye 7 may remain under constant further observation by the microscopy system, even when capturing OCT data of the retina 77.

Since the measurement beam is incident on the variable optical assembly as a parallel beam, the focal plane 15 (shown in FIG. 1) of the principal plane of the object-side beam output of the variable optical assembly 10 must be situated in the rear focal plane of the objective 29 in the second state, which is shown in FIG. 2B. As a result, the measurement beam 9 is incident on the object plane 40 in parallel. The rear focal plane is the focal plane of the objective 29 situated on that side which is further away from the eye 7.

If the eye 7 has a refractive error or if it is not accommodated, the measurement beam in the object plane 40 must have defocusing corresponding to a finite distance of the real or virtual focus from the object plane 40. By way of example, if the eye has a refractive error of +5 dpt or −5 dpt, the distance of the real or virtual focus from the object plane 40 must have a value of 200 millimeters.

In order to facilitate not only an examination of emmetropic eyes but also an examination of eyes with different refractive errors, the OCT system is embodied in such a way that the OCT system is selectively settable between a parallel beam profile in the object plane 40 and defocusing in the object plane 40, with the defocusing corresponding to a distance of the virtual or real focus from the object plane 40 which is less than 300 millimeters, less than 200 millimeters or less than 180 millimeters, less than 150 millimeters, less than 130 millimeters or less than 100 millimeters or less than 80 millimeters or less than 70 millimeters. The greater the magnitude of the refractive error of the eye to be examined is, the smaller the distance of the real or virtual focus from the object plane must be.

In order to obtain OCT data from the retina of the aphakic eye during the cataract operation, the OCT system is further embodied to set the defocusing in such a way that the distance of the real or virtual focus from the objective is greater than the distance of the object plane from the objective by a value of between 50 millimeters and 150 millimeters. Then, the virtual or real focus of the measurement beam is situated on that side of the object plane which is distant from the objective. This defocusing facilitates arranging the measurement focus on the retina in the case of an aphakic eye. it has been found that the intraocular lens to be inserted may be measured with a higher reliability by measuring the aphakic eye.

Figure 3:
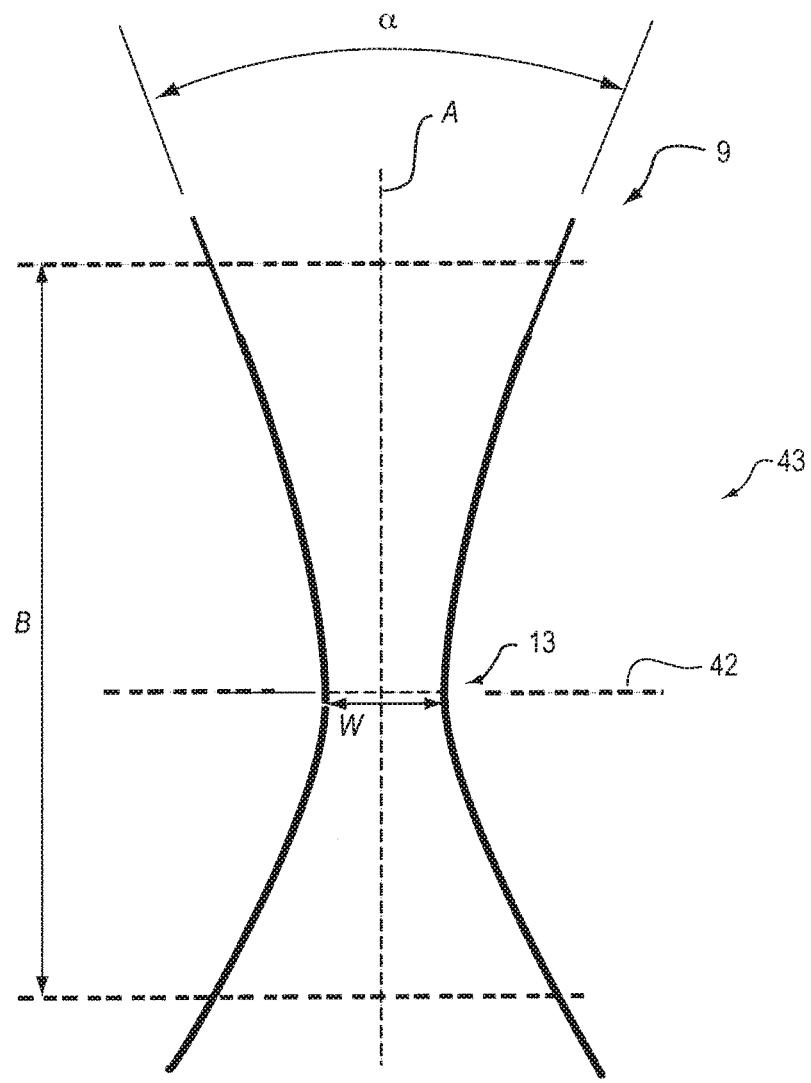
FIG. 3 illustrates the measurement focus of the OCT system of the optical system shown in FIG. 1.

The measurement focus 43 of the measurement beam 9 is depicted in detail in FIG. 3. The axial position relative to the axis A of the measurement beam 9 at which the measurement focus 43 has the tightest constriction is defined as beam waist 13. The measurement beam 9 comprises a beam waist diameter W at the beam waist 13. The beam waist 13 is moved in the scanning plane 42 by laterally scanning the measurement focus 43. The laser beam has an aperture angle α in the far field, with which the measurement beam 9 runs toward the measurement focus 43. The aperture angle α in the far field is a measure for the numerical aperture of the measurement beam at the measurement focus. The measurement focus 43, in particular the beam waist 13, is situated within an axial measurement region B of the OCT system, within which the scattering intensities are captured by the OCT system.

As already discussed with respect to FIG. 2A, the variable optical assembly is configured in such a way that an axial position of the measurement focus 43 is controllably settable along the axis A of the measurement beam 9. As a result, it is possible to arrange the measurement focus 43 at a desired position within the eye interior.

The measurement beam optical assembly is further configured in such a way that the aperture angle α of the measurement beam 9 is controllably settable for the first state and for the second state (shown in FIG. 2B). The beam waist diameter W depends on the aperture angle α in the far field. As a result, it is possible that the lateral resolution of the OCT system is settable in terms of the beam waist for selected measurement positions in the eye interior. As may be identified in FIG. 2B, the diameter d of the parallel or substantially parallel measurement beam 9-2, which is incident on the object plane 40, needs to be varied in the second state to this end. Adjusting the aperture angle or the beam diameter is explained in more detail with reference to FIGS. 4A and 4B.

It has been found that this is particularly advantageous since this renders it possible to effectively measure extended structures in the interior of the eye with the aid of the OCT system. In particular, this facilitates OCT data of a comparatively large region within the eye interior to be capturable, initially with a small aperture angle α. A small aperture angle α in the far field reduces the lateral resolution at the beam waist but facilitates the use of a large axial measurement range since the increase in the beam diameter with increasing distance from the beam waist 13 is smaller as a result of the small aperture angle α.

Then, a target region may be determined from the OCT data of the large captured region, with OCT data with a small axial measurement region B (shown in FIG. 3) being captured from said target region with a small beam waist diameter W, i.e. with a high lateral resolution at the beam waist 13. Here, the optical system in accordance with the shown exemplary embodiment facilitates modifying the lateral resolution at the beam waist without displacing the beam waist 13 along the axis A of the measurement beam 9.

The design and functionality of the variable optical assembly 10 are explained in detail with reference to FIGS. 4A to 7C.

The variable optical assembly 10 is configured in such a way that a multiplicity of different positions of the focal planes are controllably settable for a principal plane of an object-side beam output of the variable optical assembly. The focal plane positions are measured relative to a fixed reference point in this case.

As shown in FIG. 4A, the focal plane may be a virtual focal plane FP in at least some of the configurations of the variable optical assembly. In the configuration of the variable optical assembly 10 shown in FIG. 4A, a parallel incoming bundle of rays 60 produces a divergent outgoing bundle of rays 61. Therefore, the outgoing bundle of rays 61 is not focused at a real focus but appears to come from a virtual divergence point DP, which is arranged in the virtual focal plane FP of the principal plane of the object-side beam output. The focal plane FP is determined under the assumption of a parallel incident bundle of rays 60, which is incident on the variable optical assembly 10.

The portion of the measurement beam 66 (shown in FIG. 1) which is incident on the variable optical assembly 10 may be configured as a convergent beam, divergent beam, parallel beam or substantially parallel beam. Therefore, the divergence point of the emerging portion of the measurement beam 67, which emerges from the variable optical assembly 10 need not necessarily correspond with the virtual divergence point DP (shown in FIG. 4a) which emerges under the assumption of the parallel incident bundle of rays 60.

As illustrated by the comparison of FIGS. 4A and 4B, the variable optical assembly 10 is further configured in such a way that the associated focal length is controllably settable to different values for at least one of the multiplicity of focal plane positions, with the focal plane position of the focal plane FP remaining the same or substantially the same. In each of FIGS. 4A and 4B the variable optical assembly 10 is configured in such a way that the focal plane FP has the same position as measured relative to a stationary reference point. However, the associated focal lengths $f_1$ and $f_2$ are different.

In the configuration of FIG. 4B, the principal plane PP2 of the object-side beam output has a smaller distance from the focal plane FP when compared with the configuration in FIG. 4A. Further, the displacement of the principal plane is caused by moving movable optical units 11 and 12, which are described in more detail further down with reference to FIG. 5. Since the focal length is calculated from the distance between principal plane and focal plane FP, the absolute value of the focal length $f_1$ of the configuration in FIG. 4A is greater than the absolute value of the focal length $f_2$ of the configuration in FIG. 4B.

The reduced absolute value of the focal length in the configuration in FIG. 4B when compared with the configuration in FIG. 4A has as a consequence that the outgoing bundle of rays 61, which is produced by the parallel incident bundle of rays 60, has a larger aperture angle $\theta_2$ in the configuration in FIG. 4B when compared with the aperture angle $\theta_1$ in the configuration in FIG. 4A. However, the outgoing bundle of rays 61 in both configurations is such that it appears to come from a divergence point DP with the same position, arranged in the focal plane of the object-side principal plane.

A consequence of this for the measurement beam is that the aperture angle $\alpha$ in the far field (shown in FIG. 3) of the measurement beam 9 approaching the measurement focus 43 is modified, with, however, the axial measurement focal position remaining the same. Thus, a modification of the lateral resolution in the scanning plane 42 may be brought about by the different settings of the focal length in the case of a fixed position of the focal plane FP, without, however, the scanning plane 42 being displaced in terms of its axial position relative to the axis A of the measurement beam 9. This allows the surgeon to alternate easily and in a time-efficient manner between overview recordings and detailed recordings during the operation.

Further, the OCT system is configured in such a way that the variable optical assembly is controllably settable into a multiplicity of afocal or substantially afocal configurations, which have different values of an afocal beam widening. This is described below with reference to FIGS. 4C and 4D.

An afocal system shapes an emergent parallel bundle of rays 61 from an incident parallel bundle of rays 60. Therefore, the focal planes of an afocal system lie at infinity. The afocal beam widening may be defined relative to the light path directed toward the object. In particular, the beam widening may be defined as the ratio of the diameter of the object-side parallel bundle of rays to the diameter of the light-source-side parallel bundle of rays.

FIGS. 4C and 4D each show an afocal configuration, in which the variable optical assembly 10 is controllably settable. In the second configuration, which is depicted in FIG. 4D, the variable optical assembly 10 is configured in such a way that the ratio between the diameter $D_2$ of the emerging bundle of rays and the diameter of the incident bundle of rays $d_2$ (i.e. the value $D_2/d_2$) is greater than the ratio between the diameter $D_1$ of the emerging bundle of rays and the diameter $d_1$ of the incident bundle of rays of the first configuration (i.e. the value $D_1/d_1$), which is depicted in FIG. 4C. Therefore, the afocal beam widening in the second configuration is greater than in the first configuration.

Particularly if the incident portion of the measurement beam 66 (shown in FIG. 1), which is incident on the variable optical assembly 10, is configured as a parallel light beam, the greater confocal beam widening has as a consequence that the measurement beam approaches the measurement focus 43 with a greater aperture angle $\alpha$ in the far field (shown in FIG. 3). The measurement beam then has a greater numerical aperture at the measurement focus. In the optical system shown in FIG. 1, the measurement beam incident on the objective 29 in parallel is focused in the object plane 40 of the objective 29, said object plane simultaneously being the focal plane of the objective 29.

The modifiable confocal beam widening may therefore be used to modify the lateral resolution of the measurement beam 9 in the focal plane of the objective, without displacing the beam waist 42 (shown in FIG. 3) along the axis of the measurement beam 9.

FIG. 5 is a schematic view of the measurement beam optical assembly of the optical system 1, which is reproduced in FIG. 1. In order to simplify the illustration, the measurement beam 9 is shown with a straight beam axis in FIG. 5. The measurement beam 9 is emitted into the measurement beam optical assembly 22 through a light exit surface 25, which is situated at the end of an optical fiber 23. The portion of the measurement beam 9 which emerges from the light exit surface 25 is incident on a collector optical assembly 22 configured as a collimator optical assembly. The measurement beam 9 emerges from the collector optical assembly 22 as a parallel or substantially parallel beam. The portion of the measurement beam 9 which emerges from the collector optical assembly 22 enters into the scanning system 30 comprising the scanning mirrors 31 and 32, which are only reproduced very schematically in FIG. 5.

The portion of the measurement beam 9 emerging from the scanning system 30 is incident on a second movable optical unit 11. A movable optical unit may be defined in such a way that it has one or more optically effective surfaces, wherein all optically effective surfaces of the unit are movable as a unit while maintaining their arrangement relative to one another. In other words, the optically effective surfaces do not carry out a movement relative to one another when the movable optical unit is moved. The second movable optical unit 11 comprises the optically effective surfaces S1 to S5. The second movable optical unit 11 comprises a first optical subunit 26 and a second optical subunit 27, which each have positive optical refractive power and which are arranged at a distance from one another. The first optical subunit 26 is embodied as a cemented element; the second optical subunit 27 is embodied as a lens.

The portion of the measurement beam 9 emerging from the second movable optical unit 11 is incident on a first movable optical unit 12. The first movable optical unit 12 is embodied as a biconvex lens and has the optically effective surfaces S6 and S7.

The second movable optical unit 11 has positive optical refractive power. The first movable optical unit 12 has negative optical refractive power. In the afocal configuration of the variable optical assembly 10, which is depicted in FIG. 5, the portion of the measurement beam 14 emerging from the first movable optical unit 12 forms a real focus 14. The real focus 14 is situated between the first movable optical unit 12 and the third optical unit 13. The portion of the measurement beam 9 diverging from the real focus 14 is incident on the third optical unit 13. The third optical unit 13 comprises the optically effective surfaces S8 to S10. The third optical unit 13 is a stationary optical unit. However, it is also conceivable that the third optical unit 13 is a movable optical unit. The portion of the measurement beam emerging from the third optical unit 13 is incident on the deflection element 33 which is likewise only reproduced very schematically in FIG. 5. The portion of the measurement beam emerging from the deflection element 33 is incident on the objective 29. The objective 29 comprises the optically effective surfaces S11 to S13. Particularly in the afocal configurations of the variable optical assembly 10, the focal length of the third optical unit 13 is greater or 1.5-times greater or two-times greater or three-times greater than the focal length of the optical component formed by the first movable optical unit 12 and the second movable optical unit 11.

FIGS. 6A to 7C each show part of the measurement beam optical assembly, with the variable optical assembly 10 being shown in different configurations, in which the variable optical assembly is controllably settable. FIGS. 6A and 6B depict the variable optical assembly 10 in configurations in which the measurement focus 43 (shown in FIG. 3) of the measurement beam 9 is focused onto the object plane 40 of the microscopy system. Then, the beam waist 13 (shown in FIG. 3) is situated in the object plane 40. The beam path downstream of the objective 29 is parallel or substantially parallel for each of the observation channels 19-1 and 19-2 (shown in FIG. 1) of the microscopy system. Therefore, the portion of the measurement beam 9 which is incident on the objective 29 must also be parallel or substantially parallel so that the beam waist of the measurement beam 9 is arranged in the object plane 40.

In the configurations shown in FIGS. 6A and 6B, the variable optical assembly 10 is in each case configured as an afocal system which reshapes a parallel or substantially parallel incident portion 66 of the measurement beam into a parallel or substantially parallel emergent portion 67 of the measurement beam. The emergent portion 67 has a greater diameter than the incident portion 66. This brings about an increase in the numerical aperture of the portion of the measurement beam 9 which runs toward the object plane 40. The emergent portion 67 of the measurement beam 9 is incident on the objective 29 and is focused in the focal plane of the objective which is the object plane 40 of the microscopy system at the same time.

In both afocal configurations of the variable optical assembly, a first optical component consisting of the first movable optical unit 12 and the second movable optical unit 11 produces a real focus 14 within the variable optical assembly from the incident portion 66 of the measurement beam 9. Therefore, a focal plane position of a principal plane of the object-side beam output of this first optical component is arranged within the variable optical assembly. Further, this focal plane of the first optical component is arranged in a focal plane of a principal plane of a light-source-side beam input of a second optical component consisting of the third optical unit 13. This focal plane of the second optical component has a distance $f_3$ from the principal plane of the light-source-side beam input of the third optical unit 13 in both configurations.

In the configuration of FIG. 6B, the variable optical assembly 10 has a smaller beam widening when compared with the configuration of FIG. 6A. Consequently, the aperture angle $\alpha_2$ of the measurement beam, with which the measurement beam 9 runs toward the object plane 40, is smaller than the corresponding aperture angle $\alpha_1$ in the configuration of FIG. 6A. The aperture angles $\alpha_1$ and $\alpha_2$ relate to the far field of the measurement beam 9. The numerical aperture of the portion of the measurement beam which runs toward the measurement focus is determined depending on the aperture angle $\alpha_1$ and $\alpha_2$. For the configuration in FIG. 6A, this results in a numerical aperture of 0.04 and, for the configuration in FIG. 6B, this results in a numerical aperture of 0.02. Therefore, a higher lateral resolution in the beam waist may be obtained by the configuration of FIG. 6A when compared with the configuration in FIG. 6B. However, OCT scans with a great scanning depth may be carried out instead using the configuration in FIG. 6B as a result of the small numerical aperture since the increase in the beam diameter with increasing distance from the beam waist is lower as a result of the small aperture angle $\alpha_2$, when compared with the configuration in FIG. 6A.

FIGS. 7A to 7C show configurations with which the measurement focus of the measurement beam 9 is produced in the retina of the eye. In the configuration of FIG. 7A, the variable optical assembly 10 is configured in such a way that the portion 66 of the measurement beam incident on the variable optical assembly 10, which is parallel or substantially parallel, produces a portion of the measurement beam 68 emerging from the objective 29, with this emerging portion 68 being parallel or substantially parallel. As a result, the variable optical assembly 10 and the objective 29 together form an afocal or a substantially afocal system. Therefore, the light entry into the measurement beam optical assembly is imaged at infinity or a substantially at infinity by the measurement beam optical assembly. Therefore, the measurement beam 9 is incident on the object plane 40 as a parallel or substantially parallel beam and produces a measurement focus on the retina in the case of an emmetropic, non-accommodated eye.

In the configuration of FIG. 7B, a portion 66 of the measurement beam configured to be parallel or substantially parallel, which is incident on the variable optical assembly 10, leads to the measurement beam 9 being incident on the object plane 40 as a divergent beam. In the configuration depicted in FIG. 7B, a real focus 16 is produced in the region between the objective 29 and the object plane 40. The real focus 16 is a divergence point, from which the measurement beam 9 propagates freely to the object plane 40. As a result, the measurement beam in the object plane 40 has defocusing which corresponds to a focal distance $s_1$ between the real focus 16 and the object plane 40.

In the configuration depicted in FIG. 7B, the focal distance $s_1$ has a length of 200 millimeters. Therefore, the divergence of the measurement beam 9 in the object plane 40 is such that the measurement beam is focused onto the retina in the case of a non-accommodated, ametropic eye with a refractive error of −5 dpt. In order also to facilitate focusing onto the retina in the case of eyes which have a refractive error in a range between 0 dpt and −5 dpt, the variable optical assembly is controllably configurable in such a way that the measurement beam 9 has a smaller divergence in the object plane 40, i.e. a corresponding distance of a real or virtual focus from the object plane 40 is greater than the distance $s_1$ of the configuration in FIG. 7B. To this end, a real focus of the measurement beam, as seen relative to the light path directed toward the object, may also be situated in the objective 29 or upstream of the objective 29. In this case, the measurement beam 9 no longer propagates freely between the real focus and the object plane 40. Consequently, the distance between the real focus and the object plane 40 is no longer identical to the distance of the corresponding virtual focus representing the defocusing in the object plane. Expressed differently, the defocusing in the object plane 40 then corresponds to a spaced apart virtual focal point. In the case of an incident portion 66 of the measurement beam 9 configured as a parallel beam, this virtual focal point corresponds to the virtual focus of the principal plane of the object-side beam output of an optical system formed by the variable optical assembly 10 and the objective 29.

In the configuration of FIG. 7C, the measurement beam 9 is incident on the object plane 40 then in a convergent manner. The measurement beam 9 is configured in such a way that the measurement focus is situated on the retina in the case of a non-accommodated, ametropic eye with a spherical refractive error of +6 dpt. Without the presence of the eye 7, the convergent measurement beam produces a focus on that side of the object plane 40 which is distant from the objective 29, said focus having a focal distance $s_2$ from the object plane 40. Corresponding to the refractive error of +6 dpt, this focal distance has a length of 160 millimeters. The focal distance $s_2$ is only indicated schematically by the dashed arrow shown in FIG. 7c. Therefore, the defocusing of the measurement beam in FIG. 7C corresponds to a distance of a real focus from the object plane 40 with the absolute value $s_2$.

In order also to facilitate focusing onto the retina in a case of eyes which have a refractive error in a range between 0 dpt and +6 dpt, the variable optical assembly is controllably configurable in such a way that the measurement beam 9 has a smaller convergence in the object plane 40, i.e. a corresponding focal distance $s_2$ is greater.

TABLE 1

| Surface: | Radius of curvature mm | Config. FIG. 6a | Config. FIG. 6b | Config. FIG. 7a | Config. FIG. 7b | Config. FIG. 7c |
|---|---|---|---|---|---|---|
| — | — | 20.435 | 14.21 | 23.9 | 24.5 | 23.4 |
| S1 | 30 | 2.3 | 2.3 | 2.3 | 2.3 | 2.3 |
| S2 | −7.7 | 1 | 1 | 1 | 1 | 1 |
| S3 | −12.2 | 0.1 | 0.1 | 0.1 | 0.1 | 0.1 |
| S4 | 8 | 1.8 | 1.8 | 1.8 | 1.8 | 1.8 |
| S5 | — | 4.514 | 2.39 | 1.055 | 0.455 | 1.555 |
| S6 | −9.5 | 0.5 | 0.5 | 0.5 | 0.5 | 0.5 |
| S7 | 9.5 | 1.35 | 9.83 | 1.35 | 1.35 | 1.35 |
| — | — | 96.75 | 96.75 | 96.75 | 96.75 | 96.75 |
| S8 | 176.4 | 1 | 1 | 1 | 1 | 1 |
| S9 | 52.2 | 2.5 | 2.5 | 2.5 | 2.5 | 2.5 |
| S10 | −59.85 | 46 | 46 | 46 | 46 | 46 |
| S11 | 111.5 | 8 | 8 | 8 | 8 | 8 |
| S12 | −75.6 | 2 | 2 | 2 | 2 | 2 |
| S13 | −187.4 | 195.15 | 195.15 | 195.15 | 195.15 | 195.15 |
| Image | | | | | | |

The optically effective surfaces of the configurations reproduced in FIGS. 6A to 7C have the radii of curvature and distances reproduced in table 1. As presented with reference to FIG. 5, the second movable optical unit 11 comprises the optically effective surfaces S1 to S5. The first movable optical unit comprises the optically effective surfaces S6 and S7. The third optical unit comprises the optically effective surfaces S8 to S10. The objective comprises the optically effective surfaces S11 to S13.

TABLE 2

| Surface: | Diameter mm | Medium | Refractive index at 1060 nm |
|---|---|---|---|
| S1 | 9 | PSK52 | 1.5919 |
| S2 | 9 | SF57 | 1.8119 |

TABLE 2-continued

| Surface: | Diameter mm | Medium | Refractive index at 1060 nm |
|---|---|---|---|
| S3 | 9 | AIR | |
| S4 | 9 | PSK52 | 1.5919 |
| S5 | 9 | AIR | |
| S6 | 5 | LASF11 | 1.7813 |
| S7 | 5 | AIR | |
| S8 | 20 | SF57 | 1.5919 |
| S9 | 20 | PSK52 | 1.8119 |
| S10 | 20 | AIR | |
| S11 | 50 | CAF2 | 1.4285 |
| S12 | 50 | BAF3 | 1.5687 |
| S13 | 50 | AIR | |

The diameters of the optically effective surfaces, the materials of the optical elements and the refractive index which these materials have at a wavelength of the measurement beam of 1060 nanometers are reproduced in table 2.

In the configuration of FIG. 7B, the first optical component consisting of the first movable optical unit 11 and the second movable optical unit 12 produces neither a real focus nor a virtual focus within the variable optical assembly. In the configuration of FIG. 7B, the variable optical assembly is configured in such a way that the focal plane position of the principal plane of the object-side beam output of the first optical component is arranged outside of the variable optical assembly. By contrast, this focal plane is arranged within the variable optical assembly in the configurations of FIGS. 7A, 6A, 6B, 7A and 7C.

This large displaceability of the focal plane position facilitates adapting the defocusing of the measurement beam 9 in the object plane 40 to a large range of refractive errors of the eye. In particular, this allows production of the divergent measurement beam, depicted in FIG. 7B, in the object plane 40, said divergent measurement beam allowing an examination of eyes which have a refractive error of −5 dpt.

FIG. 8 illustrates the design of the collector optical assembly 22 for the OCT system of the optical system 1 depicted in FIG. 1. The collector optical assembly 22 has a modifiable focal length. The focal length of the collector optical assembly 22 is controllably modifiable in such a way that the portion 69 of the measurement beam 9 which emerges from the collector optical assembly 22 is parallel in each case for various values of the focal length. A diameter of the portion 69 is different in each case for the different values of the focal length. Therefore, the various values of the focal length of the collector optical assembly cause different values of the numerical aperture of the portion of the measurement beam 9 running toward the measurement focus 43.

This embodiment of the collector optical assembly 22 facilitates the optimization of the variable optical assembly for the function of changing the actual measurement focus position as the variable optical assembly no longer needs to assume the function of setting the numerical aperture. The displacement of the measurement focus along the axis of the measurement beam is then caused by the actuation of the variable optical assembly; however, the numerical aperture of the measurement beam at the measurement focus is set by actuating the collector optical assembly. By dividing these two functions among two separate optical systems, it is possible to obtain extended ranges for setting the axial measurement focus position and/or the numerical aperture.

Moreover, this facilitates a more compact design of the variable optical assembly, causing space to be saved in the surrounding region of the objective. Moreover, as a result of this, the measurement beam 9 is guided through the scanning system 30 as a parallel beam rather than a convergent or divergent beam. This prevents the image quality of the OCT data from being impaired by Doppler effects if the scanning mirrors are not aligned perfectly relative to one another. Further, this avoids the relationship between the scanning position and the rotational angle of the mirrors being different for the scanning mirrors.

FIG. 8 shows the design of the collector optical assembly 22. The collector optical assembly 22 reshapes a portion of the measurement beam, which emerges from the light exit surface 25 of the optical fiber 23, into a portion 69 of the measurement beam 9, which emerges from the collector optical assembly 22 and which is parallel for various values of a settable focal length of the collector optical assembly 22.

As shown in FIG. 8, the collector optical assembly 22 comprises a first movable optical unit 72 and a second movable optical unit 73. The first movable optical unit 72 has negative refractive power. The second movable optical unit 73 has positive refractive power. As seen relative to the light path of the measurement beam 9 directed toward the object, the second moveable optical unit 73 is disposed downstream of the first movable optical unit 72. The measurement beam 9 leaves the collector optical assembly 22 through the second movable unit 73. The portion 69 of the emergent measurement beam 9 is parallel in each case for various values of the settable focal length of the collector optical assembly 22.

The collector optical assembly 22 comprises a third optical unit 71, which is disposed upstream of the first movable unit 72. The third optical unit 71 has positive refractive power. Moreover, the collector optical assembly 22 comprises a fourth optical unit 70. The fourth optical unit 70 is disposed upstream of the third optical unit 71 and likewise has positive refractive power. The measurement beam 9 enters the collector optical assembly 22 through the fourth optical unit 70. A portion 75 of the measurement beam 9 which emerges from the fourth optical unit 70 is parallel. A stop 74 is arranged between the fourth optical unit 70 and the third optical unit 71.

The collector optical assembly 22 is configured in such a way that, for various values of the focal length of the collector optical assembly, a diameter of the portion 69 of the measurement beam 9 which emerges from the collector optical assembly 22 is controllably settable to various values. For the various values of the diameter, the portion 69 of the measurement beam 9 which emerges from the collector optical assembly 22 is parallel. As a result, various values of the numerical aperture are settable at the measurement focus, with the measurement beam 9 passing through the scanning device 30 (shown in FIG. 1) as a parallel beam for each of the various values.

TABLE 3

| Surface | Radius (mm) | Thickness (mm) Zoom 1 | Zoom 2 | Zoom 3 | Diameter (mm) | Glass | Refractive index at 1060 mm |
|---|---|---|---|---|---|---|---|
| — | — | 4.52 | 4.52 | 4.52 | | Air | 1.0000 |
| S15 | 5.54 | 0.50 | 0.50 | 0.50 | 2.00 | SF57 | 1.8119 |
| S16 | 2.30 | 0.80 | 0.80 | 0.80 | 2.00 | PSK52 | 1.5919 |
| S17 | −3.80 | 1.00 | 1.00 | 1.00 | 2.00 | AIR | 1.0000 |
| S18 | 12.65 | 0.80 | 0.80 | 0.80 | 3.20 | PSK52 | 1.5919 |
| S19 | −25.00 | 7.171 | 4.95 | 0.511 | 3.20 | AIR | 1.0000 |
| S20 | −7.32 | 0.50 | 0.50 | 0.50 | 2.00 | SF57 | 1.8119 |
| S21 | 7.32 | 0.511 | 4.95 | 7.171 | 2.00 | AIR | 1.0000 |
| S22 | 25.00 | 0.80 | 0.80 | 0.80 | 3.20 | PSK52 | 1.5919 |
| S23 | −12.65 | 2.218 | 0 | 2.218 | 3.20 | AIR | 1.0000 |

The optical effective surfaces of the collector optical assembly 22, which are reproduced in FIG. 8, have the radii of curvature, distances and diameters reproduced in table 1. Further, table 1 reproduces the materials of the optical elements and the refractive indices which these optical elements have at a wavelength of the measurement beam of 1060 nanometers. The first movable optical unit 72 comprises the optically effective surfaces S20 and S21. The second movable optical unit 73 comprises the optically effective surfaces S22 and S23. The third optical unit 71 comprises the optically effective surfaces S18 and S19. The fourth optical unit 70 comprises the optically effective surfaces S15, S16 and S17. The fourth optical unit 70 may be embodied as a cemented element.

Figure 9A:
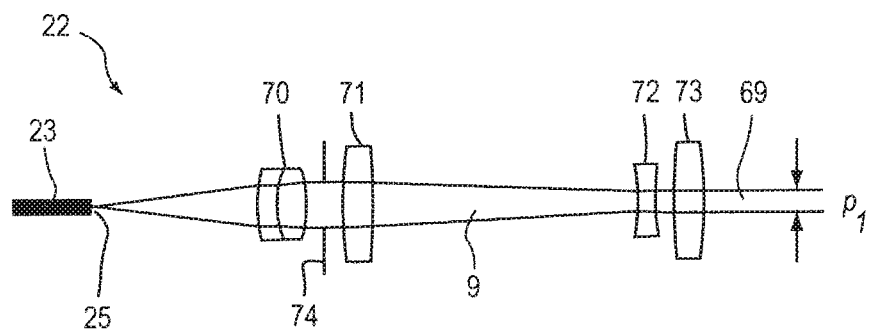
FIGS. 9A to 9C illustrate various settings of the collector optical assembly shown in FIG. 8, by means of which different diameters of the emerging parallel measurement beam are producible.
Figure 9B:
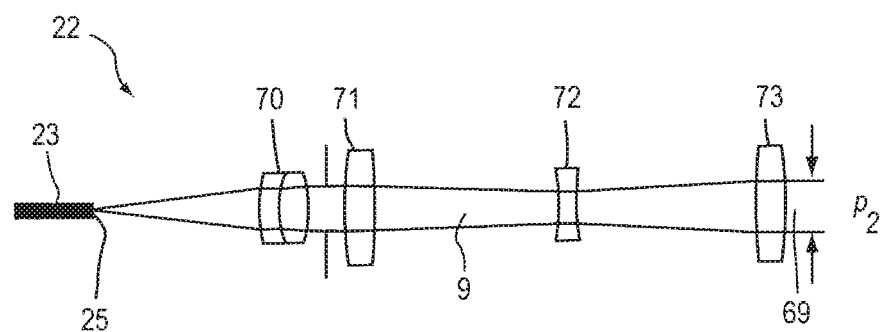
Figure 9C:
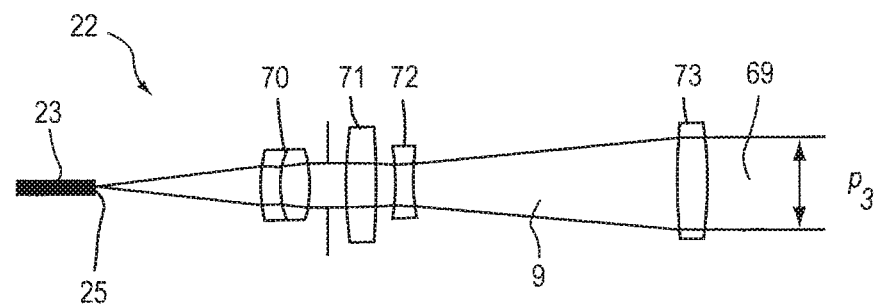

FIGS. 9A to 9C show three configurations of the collector optical assembly 22 for producing different diameters of the parallel emergent portion 69 of the measurement beam. The configuration of the collector optical assembly 22 shown in FIG. 9A produces a diameter $p_1$ with a value of 0.36 millimeters. The configuration of the collector optical assembly 22 shown in FIG. 9B produces a diameter $p_2$ with a value of 0.72 millimeters. The configuration of the collector optical assembly 22 shown in FIG. 9C produces a diameter $p_3$ with a value of 1.44 millimeters.

As shown in FIG. 1, the optical system 1 comprises a fixation light device 87 for producing a real or virtual fixation point for the eye. The patient with the eye 7 to be examined may look at the real or virtual fixation point, in particular if the eye is positioned in such a way that the cornea is situated in the object plane 40. By looking at the fixation point, the eye 7 fixates centrally onto the fixation point. In the case of central fixation, the image of the fixation point is situated in the middle of the foveola of the eye 7. Micro-movements of the eye are ignored here. The foveola is the region of sharpest vision within the fovea. The diameter of the foveola is approximately 0.33 millimeters.

The fixation point may be defined by a real or virtual image produced by the fixation light device 87. By way of example, the real or virtual image may be cross hairs or a circle. Then, for example, the fixation point may be the center of the cross hairs or the center of the circle.

The fixation light device 87 comprises a fixation light unit 80. The fixation light unit 80 comprises a fixation light source which produces a fixation light 81, which is deflected onto the objective 29 by a deflection element 82. The fixation light 81 passes through the objective 29. It is conceivable for the fixation light also to pass through the variable optical assembly 10. By way of example, the fixation light source may comprise an LED and/or a laser. The fixation light 81 may have a light wavelength in the visible spectrum, by means of which the patient may easily distinguish the fixation light 81 from the illumination light of an object plane illumination (not shown in FIG. 1) of the optical system 1. By way of example, this light wavelength may lie in the green spectral range. Alternatively, or additionally, the optical system 1 may be configured in such a way that the intensity of the fixation light 81 changes in accordance with a temporal pattern. By way of example, the intensity of the fixation light 81 may increase and decrease periodically in time and/or the fixation light 81 may be temporally triggered. By way of example, a temporally triggered fixation light may be a blinking fixation light.

The real or virtual fixation point produced by the fixation light device 87 has a large distance from the object plane 40. Therefore, the visual axis of the eye 7 is aligned along a defined visual axis direction, to be precise substantially independently of the position of the eye in a direction perpendicular to the visual axis direction, in the case of central fixation of the fixation point.

In the optical system 1 depicted in FIG. 1, the fixation light 81 is configured in such a way that this defined visual axis direction extends parallel to the optical axis OA of the objective 29. Further, the OCT system 2 is configured in such a way that the axis of the measurement beam 9 extends along the optical axis OA of the objective 29.

This facilitates a precise measurement of the anterior chamber depth, the lens thickness and the axial length of the eye. This is explained below with reference to FIGS. 10A and 10B.

Figure 10A:
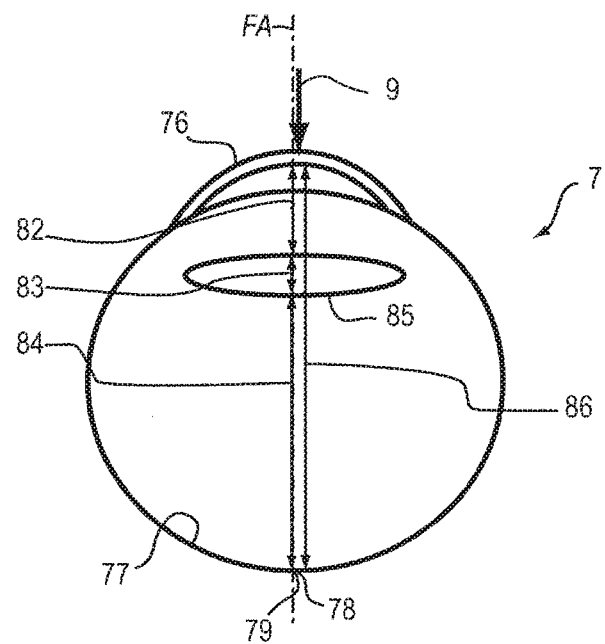
FIGS. 10A and 10B illustrate the measurement of anatomical parameters of the eye in the state of central fixation using the optical system shown in FIG. 1.

FIG. 10A shows the eye 7 in a state in which the fixation point is fixated centrally. The fixation visual axis of the eye, i.e. the visual axis of the eye in the state of central fixation, is denoted by the reference sign FA. In this state, the image 79 of the fixation point is situated in the center of the foveola 78. The fixation visual axis FA is defined as the connecting line between the center of the foveola 78 and the fixation point when the eye is in the state of central fixation.

The eye is positioned relative to the optical system in such a way that, in the case of a scanning setting of the scanning system, an axis of the incident portion of the measurement beam 9 extends along or substantially along the fixation visual axis FA. This facilitates ascertaining a multiplicity of anatomical parameters with high precision by means of OCT measurements, such as e.g. the anterior chamber depth 82, the lens thickness 83, the distance 84 between the posterior lens capsule 85 and the retina 77, and the axial length 86 of the eye 7.

Figure 10B:
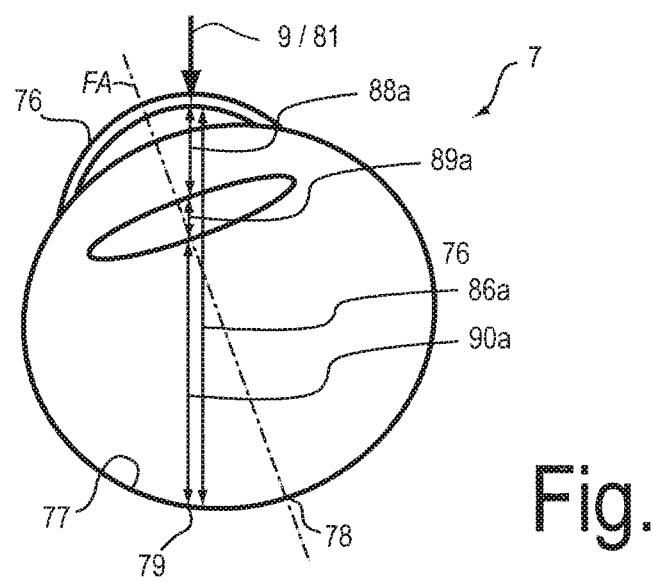

In comparison with FIG. 10A, FIG. 10B shows the eye in a state in which the fixation point is not fixated centrally. The image 79 of the fixation point then is situated away from the center of the foveola 78. As may be identified on the basis of FIG. 10B, the lengths 88*a*, 89*a*, 90*a* and 86*a* measured along the axis of the measurement beam 9 then deviate from the anatomical parameters, depicted in FIG. 10A, of the anterior chamber depth 82, the lens thickness 83, the distance 84 between the posterior lens capsule 85 and the retina 77, and of the axial length 86 of the eye 7.

Figure 11A:
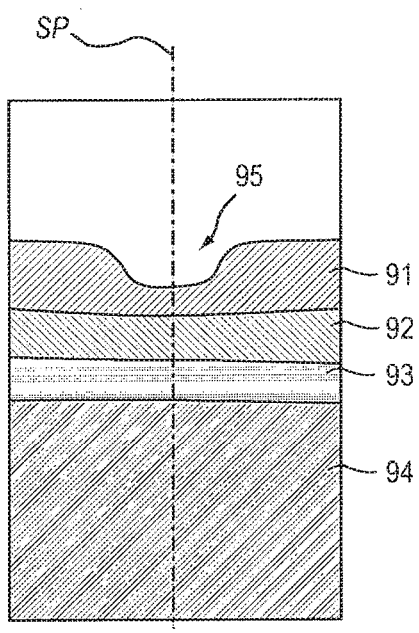
FIGS. 11A and 11B illustrate checking the state of the central fixation in a manner dependent on OCT data which were captured by the retina.
Figure 11B:
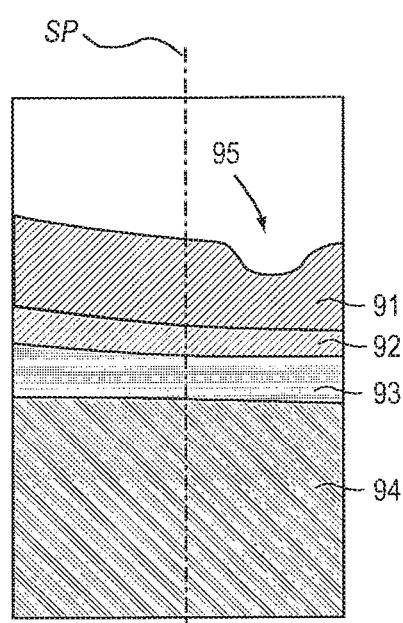

As explained in relation to FIGS. 11A and 11B, the optical system is embodied in such a way that the state of the central fixation may be checked depending on captured OCT data of the retina.

FIG. 11A shows a first B-scan, which reproduces a cross section through the upper layers 91, 92, 93, 94 of the retina. The OCT data in FIG. 11A were captured in the state reproduced in FIG. 10A, i.e. in a state in which the fixation point is centrally fixated by the eye. The B-scan may represent a part of a volume scan. The cross section is configured in such a way that it contains the image of the foveola center. Therefore, the depression 95 of the fovea, which represents the foveola, may be identified in the B-scan. The center of the foveola is situated at a scanning position SP.

FIG. 11B shows a second B-scan, at the same scanning positions as in FIG. 11A. However, the OCT data in FIG. 11B were captured in the state of the eye reproduced in FIG. 11B, and in which the fixation point is not centrally fixated by the eye.

Therefore, the center of the foveola does not appear at the scanning position SP, as reproduced in the OCT data in FIG. 11A, in the OCT data which are reproduced in FIG. 11B. Consequently, a check may be carried out on the basis of the OCT data as to the whether the eye is in a state in which the fixation point is centrally fixated.

The optical system is embodied to determine dependent on the OCT data whether the image of the center of the foveola is situated at the scanning position SP and/or whether a deviation of the image of the center of the foveola from the scanning position SP is within a predetermined threshold. As a result, it is possible to determine whether parameters which were captured by measurements on the eye lie within a required accuracy. The OCT data may represent a two-dimensional scan or a volume scan.

By way of example, the scanning position SP may be determined by virtue of OCT data of the retina being captured over a relatively long period of time, during which the fixation light is activated. When the fixation light is activated, the eye is predominantly in a state of central fixation. If the eye is emmetropic and non-accommodated, the scanning position SP is the one in which the axis of the portion of the measurement beam incident on the eye extends parallel to the fixation visual axis. In the system depicted in FIG. 1, this then is the scanning position at which the measurement beam 9 extends along the optical axis.

Consequently, the optical system easily facilitates checking the state of the central fixation dependent on captured OCT data of the retina. In particular, this allows the anatomical parameters depicted in FIG. 10A to be determined reliably during a cataract operation.

When checking the state of the central fixation dependent on the OCT data, the measurement focus need not necessarily be situated in the region of the retina. It is conceivable to capture OCT data of anatomical structures, to be measured, within the eye at the same time as OCT data of the retina. By way of example, such an anatomical structure may be the natural lens. Here, the measurement focus may be situated away from the retina, for example in the natural lens or in the region between the natural lens and the retina, with the axial measurement region however reaching up to the retina.

Then, depending on the OCT data, it is firstly possible to measure the anatomical structure and secondly possible to check whether the eye is in the state of central fixation. Here, the optical system in accordance with the exemplary embodiment allows appropriate configuration of the axial position of the measurement focus and/or of the numerical aperture at the measurement focus by actuating the variable optical assembly and/or by actuating the collector optical assembly.

For the purposes of measuring the eye length, it is alternatively also conceivable to capture OCT data at different times such that the data represent different states of the eye.

In the case of an appropriate selection of the number and temporal intervals of the different times, the measurement values then represent the axial length 86 (shown in FIG. 10A) in the state of central fixation 86 and, secondly, measurement values in states which deviate from the central fixation, like the measurement value 86a (shown in FIG. 10B). It has been found that the measured values are at a maximum in the state of central fixation. Thus, if measurement values are captured over a relatively long period of time, the maximum values represent the axial length of the eye. The fixation light may be switched off for capturing comparison values in which the eye is not in the state of central fixation.

The invention claimed is:

1. An optical system for examining an eye, wherein the optical system comprises:
   an OCT system configured to produce a measurement beam which is incident on the eye;
   wherein the OCT system comprises an objective and a variable optical assembly, wherein the variable optical assembly is disposed upstream of the objective when seen relative to a light path of the measurement beam directed toward the object;
   wherein the variable optical assembly has a first optical component having an optically effective entry surface, through which the measurement beam, in the light path directed toward the object, enters into the variable optical assembly and wherein the first optical component further comprises a focal plane of a principal plane of an object-side beam output of the first optical component;
   wherein the variable optical assembly has a second optical component comprising an optically effective exit surface of the variable optical component, through which the measurement beam, in the light path directed toward the object, leaves the variable optical component;
   wherein the variable optical assembly is configurable into a first configuration in a controllable manner, in which a focal plane position of the first optical component is situated within the variable optical assembly;
   wherein the variable optical assembly is configurable into a second configuration in a controllable manner, in which the focal plane position of the first optical component is situated outside of the variable optical assembly; and
   wherein the variable optical assembly is re-configurable between the first configuration and the second configuration by displacing at least one movable optical unit along the light path directed toward the object.

2. The optical system as claimed in claim 1, wherein the first optical component has a controllably modifiable focal length.

3. The optical system as claimed in claim 1, wherein the variable optical assembly is a substantially afocal system in the first configuration.

4. The optical system as claimed in claim 1, wherein, in the first configuration, a second optical component of the variable optical assembly images a point at the focal plane position of the first optical component substantially at infinity on the object side.

5. The optical system as claimed in claim 1, wherein the variable optical assembly further comprises a second optical component which, relative to a light path of the measurement beam directed toward the object, is disposed downstream of the first optical component;
   wherein, in the first configuration, a focal length of a principal plane of a light-source-side beam path of the second optical component is 1.5-times greater than a focal length of the principal plane of the object-side beam output of the first component.

6. The optical system as claimed in claim 1,
   wherein the variable optical assembly further is configurable into a second configuration in a controllable manner, in which the focal plane position of the first component is situated outside of the variable optical assembly;
   wherein a focal length of the principal plane of the object-side beam output of the first optical component is greater in the second configuration than in the first configuration.

7. The optical system as claimed in claim 1, wherein the optical system comprises a fixation light device for producing a fixation point for an eye, arranged at a position of an object distance from the objective, wherein the object distance has a value of between 50 millimeters and 400 millimeters.

8. The optical system as claimed in claim 7, wherein the OCT system comprises a scanning system, wherein, in the case of a scanning setting of the scanning system, an axis of the measurement beam extends substantially parallel to a visual axis of the eye when the eye centrally fixates the fixation point.

9. The optical system as claimed in claim 1, further comprising a microscopy system configured to produce an observation channel, wherein, with the aid of the observation channel, an image of an object region of the eye is producible in an image plane, said object region being arranged in an object plane;
   wherein the observation channel passes through the objective and the object plane is situated at the position of the object distance.

10. The optical system as claimed in claim 1, wherein a multiplicity of different focal plane positions are controllably settable for a principal plane of an object-side beam output of the variable optical assembly by means of actuating the variable optical assembly.

11. The optical system as claimed in claim 1, wherein a focal length of a principal plane of an object-side beam output of the variable optical assembly is controllably settable to different values, wherein a focal plane position of the principal plane is substantially the same at each one of the values.

12. The optical system as claimed in claim 1, wherein the variable optical assembly is controllably adjustable to a multiplicity of substantially afocal configurations, which have different values of afocal beam widening.

13. An optical system for examining an eye by means of optical coherence tomography (OCT), wherein the optical system comprises:
   an OCT system configured to produce a measurement beam which is incident on the eye;
   wherein the OCT system comprises an objective and a variable optical assembly, wherein the variable optical assembly is disposed upstream of the objective when seen relative to a light path of the measurement beam directed toward the object;
   wherein a multiplicity of different focal plane positions are controllably settable for a principal plane of an object-side beam output of the variable optical assembly by means of actuating the variable optical assembly; and wherein the optical system is further configured in such a way that the focal length of the principal plane of the object-side beam output of the variable optical assembly is controllably settable to different values for at least one of the focal plane positions, wherein the at least one of the focal plane positions is the same for each one of the different values of the focal length of the principal plane of the object side beam output of the variable optical assembly; and/or that the variable optical assembly is controllably adjustable to a multiplicity of substantially afocal configurations, which have different values of afocal beam widening.

14. The optical system as claimed in claim 13, wherein the optical system is configured or configurable in such a way that the measurement beam is incident on the variable optical assembly as a substantially parallel beam.

15. The optical system as claimed in claim 13, wherein the OCT system comprises a scanning system for scanning the measurement beam, wherein the scanning system, as seen relative to a light path of the measurement beam directed toward the object, is disposed upstream of the variable optical assembly.

16. The optical system as claimed in claim 13, wherein the OCT system comprises a scanning system for scanning the measurement beam, wherein the scanning system, as seen relative to a light path of the measurement beam directed toward the object, is disposed downstream of the variable optical assembly.

17. The optical system as claimed in claim 13, wherein the variable optical assembly comprises a first movable optical unit.

18. The optical system as claimed in claim 17, wherein the first movable optical unit has negative refractive power.

19. The optical system as claimed in claim 13, wherein the variable optical assembly comprises a second movable optical unit, wherein the second movable optical unit has positive refractive power, and/or the measurement beam enters into the variable optical assembly through the second movable optical unit.

20. The optical system as claimed in claim 13, wherein the variable optical assembly comprises a first movable optical unit and a second movable optical unit, wherein the first movable optical unit has negative refractive power and the second movable optical unit has positive optical refractive power;

wherein, as seen relative to the light path of the measurement beam directed toward the object, the first movable optical unit is disposed downstream of the second movable optical unit.

21. The optical system as claimed in claim 13, wherein the variable optical assembly comprises a third optical unit, wherein the third optical unit, as seen relative to a light path of the measurement beam directed toward the object, is disposed downstream of a first movable optical unit, having negative refractive power, of the variable optical assembly; and/or is disposed downstream of a second movable optical unit, having positive refractive power, of the variable optical assembly; and/or the measurement beam leaves the variable optical assembly through the third optical unit; and/or the third optical unit has positive refractive power; and/or a position of a focal plane of a principal plane of a light-source-side beam input of the third optical unit is arranged within the variable optical assembly.

* * * * *